US011164677B1

(12) United States Patent
Harris et al.

(10) Patent No.: US 11,164,677 B1
(45) Date of Patent: Nov. 2, 2021

(54) SYSTEM, METHOD AND CONTAINER DELIVERY SYSTEM FOR MANIPULATING THE FUNCTIONING OF A TARGET

(71) Applicant: SpinQ Biophysics, Inc., Jackson, WY (US)

(72) Inventors: Marc Harris, Bozeman, MT (US); Deni Hogan, Jackson, WY (US)

(73) Assignee: SpinQ Biophysics, Inc., Jackson, WY (US)

( * ) Notice: Subject to any disclaimer, the term of this patent is extended or adjusted under 35 U.S.C. 154(b) by 0 days.

(21) Appl. No.: 17/151,564

(22) Filed: Jan. 18, 2021

(51) Int. Cl.
*G06N 10/00* (2019.01)
*G16H 50/50* (2018.01)
*H01L 49/00* (2006.01)
*G01N 33/68* (2006.01)

(52) U.S. Cl.
CPC ............. *G16H 50/50* (2018.01); *G06N 10/00* (2019.01); *H01L 49/006* (2013.01); *G01N 33/6848* (2013.01)

(58) Field of Classification Search
CPC .................................................... G61H 50/50
USPC ............................................................. 435/5
See application file for complete search history.

(56) References Cited

U.S. PATENT DOCUMENTS

| | | | | |
|---|---|---|---|---|
| 5,898,720 | A * | 4/1999 | Yamamoto | H01S 3/16 372/39 |
| 6,597,010 | B2 * | 7/2003 | Eriksson | B82Y 10/00 257/14 |
| 9,232,618 | B2 * | 1/2016 | Bourke, Jr. | H01J 65/042 |
| 9,645,141 | B2 * | 5/2017 | Lee | G01N 33/54326 |
| 9,796,748 | B2 * | 10/2017 | Schaus | C12Q 1/16 |
| 2010/0113983 | A1 | 5/2010 | Heckerman et al. | |
| 2013/0266328 | A1 * | 10/2013 | Paller | H04B 10/25 398/135 |

OTHER PUBLICATIONS

Flatte, "Semiconductor Spintronics for Quantum Computation", Proceedings of the NATO Advanced Study Institute on Manipulating Quantum Coherence in Solid State Systems, Cluj-Napoca, Romania, Aug. 29-Sep. 8, 2005, pp. 1-52.*
https://www.mdpi.com/2076-3417/10/11/4053/htm, accessed Jan. 21, 2021.
https://www.nature.com/articles/s41401-020-0483-6#Tab2, accessed Jan. 21, 2021.
https://pubmed.ncbi.nlm.nih.gov/33083808/, accessed Jan. 21, 2021.
https://pubs.acs.org/doi/10.1021/bi00328a027, accessed Jan. 21, 2021.
https://heidolph-instruments.com/en/products/Shakers-Mixers/Multi-Reax~p1189, accessed Jan. 21, 2021.
V. N. Binghy, "Interference of Ion Quantum States Within a Protein Explains Weak Magnetic Field's Effect on Biosystems", Electro- and Magnetobiology, 1997, p. 203-214.
V. N. Binghy at el, "Molecular Gyroscopes and Biological Effects of Weak Elf Magnetic Fields", p. 2-10.
Neill Lambert at el, "Quantum biology", Nature Physics, vol. 9, Jan. 2013, p. 10-18.
"Quantum Coherence in Biological Systems", International Symposium, Nanoscience and Quantum Physics, vol. 302, p. 1-5, Jan. 2011.
Graham R. Fleming at el, "Quantum Effects in Biology", Procedia Chemistry 3, 2011, p. 38-57.
Vahid Salari, "Quantum Interference and Selectivity Throughbiological Ion Channels", Scientific reports, p. 1-25, Jan. 30, 2017.
Markus Arndt at el, "Quantum Physics Meets Biology", HFSP Journal, 2009, p. 386-400.
Irina Basieva at al, "Quantum-Like Interference Effect in Gene Expression: Glucose-Lactose Destructive Interference", System and synthetic Biology, Mar. 20, 2011.
Hia-Xia Su at el, "Anti-SARS-Cov-2 Activities In Vitro of Shuanghuanglian Preparations and Bioactive Ingredients", Acta Pharmacologica Sinica, Jul. 31, 2020, p. 1-36.
https://news.stanford.edu/2021/01/14/new-state-matter-one-dimensional-quantum-gas/, accessed Feb. 11, 2021.
https://medlineplus.gov/genetics/understanding/genomicresearch/genomeediting/, accessed Feb. 11, 2021.

* cited by examiner

Primary Examiner — Phillip A Johnston
(74) Attorney, Agent, or Firm — Quinn IP Law

(57) ABSTRACT

A system, method, diagnostic and container delivery system for manipulating a target, by manipulating with the quantum coherence of the target. The method includes identifying intrinsic parameters of the target and determining target-tuned design factors based at least partially on the intrinsic parameters. Target-tuned electrons and fields are generated based in part on the target-tuned design factor. The target-tuned electrons and fields are defined by discrete quantized energy levels. The method may include preparing a container to carry the unquantized target-tuned electrons, the container being composed of superconductor quantum dots. The unquantized target-tuned electrons are transferred to the container to form target-tuned artificial atoms having quantized target-tuned electrons, which may be delivered to the target as a manipulating agent. Alternatively, the unquantized target-tuned electrons may be delivered directly to the subject.

20 Claims, 10 Drawing Sheets

SYSTEM, METHOD AND CONTAINER DELIVERY SYSTEM FOR MANIPULATING THE FUNCTIONING OF A TARGET

INTRODUCTION

The disclosure relates generally to manipulating the functioning of a target by manipulating the quantum coherence of the target. More specifically, the disclosure relates to a system and method of identifying, generating and delivering target-tuned electrons in the form of target-tuned artificial atoms to manipulate the quantum coherence and functioning of a target, as well as a diagnostic and nanostructure container delivery system. Throughout history, living organisms have been challenged by infections, illnesses, and diseases. It is certainly not a trivial matter to treat and prevent conditions due to their various, vast, and complex underlying factors. Three items that highlight this complexity and urgency for new biotechnology include antimicrobial resistance, Covid-19 (SARS-CoV-2) and rare diseases. The UN Ad hoc Interagency Coordinating Group on Antimicrobial Resistance has warned, without action, drug-resistant diseases could cause 10 million deaths each year by 2050 with damage to the economy as catastrophic as the 2008-2009 global financial crisis. With the CDC reporting more than 2.8 million infections and 35,000 deaths occurring annually in the US. The current Covid-19 (SARS-CoV-2) pandemic has boldly highlighted the complex coupling between systems in the US and throughout the world with cascading systemic failures that have had catastrophic consequences. SARS-CoV-2 has additionally highlighted the complex nature of diseases when weighed against preexisting conditions, unknown preexisting risk, and the complex and fatal nature of immune responses when a novel virus can proliferate through a population with exponential growth. This is complicated further by viral mutations that occur as the virus persists in a population. If only a few percent of infected people develop untreatable "Long Covid" chronic symptoms—fatigue, chest pain, cognitive dysfunction, dyspnea—that amounts to hundreds of thousands of future patients. This will indubitably impact additional healthcare infrastructures. Virus mutations and viruses jumping across species, including into humans, are a normal part of natural selection. This has happened in the past. It will happen again in the future. Lastly, rare diseases are complex; with over 7,000 such conditions known, with 50% of those affected being children, with many of the disorders being exceptionally rare. The costs of rare diseases are a stubborn, significant issue. According to *PharmaTimes Online*, (27 Feb. 2020), "Parents and patients are building biotech companies, advocacy groups, technology platforms and data models and these are the new pioneers that sit alongside the medical and science community."' (*PharmaTimes Online*, 27 Feb. 2020.) This biotech company is in the afore-mentioned group. This quantum molecular biophysics biotechnology on the surface focuses on the dynamics of biological assemblies, structures and functioning from both molecular biophysics and quantum biology.

SUMMARY

Presented herein is a system, method, diagnostic and nanostructure container for manipulating the quantum coherence of the target. A method for manipulating quantum coherence in a target includes identifying intrinsic parameters of a target and calculating target-tuned design factors based at least partially on the intrinsic parameters. A target-tuned quantum electron field, in the form of unquantized target-tuned electrons, is generated based in part on the target-tuned design factors. The method may include preparing a container to carry, deliver and quantize the target-tuned electrons into target-tuned artificial atoms (embedded with quantized target-tuned electrons), with the container being composed of superconductor quantum dots (sQD). The method includes transferring the unquantized target-tuned electrons to the container to form target-tuned artificial atoms with quantized target-tuned electrons, the target-tuned artificial atoms defining discrete quantized energy states. The quantized target-tuned electrons may be delivered to the subject in the form of target-tuned artificial atoms. The target-tuned artificial atoms are employed as a manipulating agent to manipulate the quantum coherence in the target. The target-tuned artificial atoms are employed as a manipulating agent to manipulate the quantum coherence in the target. Alternatively, the unquantized target-tuned electrons may be delivered directly to the subject.

In some embodiments, at least one of the intrinsic parameters and the target-tuned design factors is a mass-to-charge ratio and the device is a mass spectrometer. The target-tuned artificial atoms are target-tuned in order to manipulate the quantum coherence in the target to induce quantum decoherence, the quantum decoherence being perceived as collapsing the respective wave functions of an electron field quantum coherence of the target. In some embodiments, the target is a virus having at least one cellular membrane docking structure, the manipulating agent being adapted to inhibit at least one viral docking structure from docking into a cell receptor of a subject.

In some embodiments, the container is an engineered clathrate hydrate that is tunable, the engineered clathrate hydrate having a plurality of nodes and a hollow interior portion with an inner lining of positive charges. The target-tuned quantum electron field is stored in and contained by the inner lining of positive charges in the engineered clathrate hydrate. Preparing the container includes applying a first predetermined electromagnetic induction to a solution of distilled water to induce quantum coherence within the distilled water to form an engineered clathrate structure, via a magnetic field generator, the engineered clathrate structure having a hollow interior portion.

Creating the container and inducting the container with the target-tuned electrons may include exposing the solution to an electromagnetic field or magnetic field until the hollow interior portion of the engineered clathrate hydrate has an inner lining of positive charges and an exterior portion of the engineered clathrate hydrate is at least partially lined with negative charges and creating cooper pairs. The unquantized target-tuned electrons are generated within the solution via a frequency transfer device. The method may include transferring the unquantized target-tuned electron field into the hollow interior portion of the engineered clathrate hydrate by applying a first vibration to the solution in order to attract and capture the unquantized target-tuned electrons within the inner lining of positive charges and form the quantized target-tuned electrons.

The method may include applying a second vibration to the target-tuned artificial atoms in order to expose the quantized target-tuned electrons from within the inner lining of positive charges in the engineered clathrate hydrate; and delivering the target-tuned artificial atoms as the manipulating agent to a subject. The second vibration may include exactly 10 vibrations. The engineered clathrate hydrate may define an original state with the plurality of nodes being separated by a first interatomic spacing and a compressed state with the plurality of nodes being separated by a second interatomic spacing. The first interatomic spacing and the second interatomic spacing may be approximately 4.68 Angstrom and approximately 3.91 Angstrom, respectively. The method further includes stabilizing the engineered clathrate hydrate from an original state into a compressed state by exposing the original state to a second predefined magnetic field. In one example, the original state is a tetrahedral clathrate and the compressed state is a hexa-kai-decahedral clathrate.

Delivering the manipulating agent may include applying the manipulating agent sublingually to the subject. Delivering the manipulating agent may include at least one of providing the manipulating agent through delivery routes within each of oral, sublingual, pulmonary, transdermal, ocular, otic, nasal, inhalation, vaginal, rectal, dialysis, nebulization, inhalation, cutaneous, subcutaneous, directly, and injection. The quantized target-tuned electrons may be based on a calibration factor, the method further including determining if a mass spectrum peak correlated to the target zone is removed or adjusted, via a validation process; and adjusting the calibration factor and repeating the validation process if the target zone mass spectrum peak is not removed or adjusted.

In some embodiments, the target is a SARS-CoV-2 virus, the target zone is the SARS-CoV-2 Nucleocapsid, the intrinsic factor is an energy-pattern of a Qsphere vector of 375 volts based on an ion mass of 375 m/z; and the target-tuned electron energy-pattern is characterized by the energy pattern of the Qsphere vector of 3.75 femtovolts ($3.75 \times 10^{-15}$ V) and a quantum energy-state of femtovolts. Generating the target-tuned artificial atoms includes at least one of: generating an attovolt quantum energy-state with a work-state in an attovolt region ($1 \times 10^{-18}$ volts through $1 \times 10^{-20}$); generating a femtovolt quantum energy-state with a work-state in a femtovolt region ($1 \times 10^{-15}$ volts through $1 \times 10^{-17}$); generating a picovolt quantum energy-state with a work-state in a picovolt region ($1 \times 10^{-12}$ volts through $1 \times 10^{-14}$); and generating a nanovolt quantum energy-state and work state in the nanovolt region ($1 \times 10^{-9}$ through $1 \times 10^{-11}$). The method includes inducing a voltage of the electron field at a magnitude determined by the target-tuned design factor. Generating the target-tuned artificial atoms may include adapting a function generator to generate target-tuned solitons, the target-tuned solitons being in a quantum energy-state less than 14.1 Angstroms.

In some embodiments, the target is a SARS-CoV-2 virus. The target zone may be a nucleocapsid protein (N-protein), the manipulating agent being adapted to neutralize the SARS-CoV-2 virus in a viral infection. The target zone may be a spike protein (S-protein), the manipulating agent being adapted to induce target zone structural bond reordering and shape change in the S-Protein of the SARS-CoV-2 virus. the target-tuned electron energy-pattern is characterized by an energy pattern of about 30 picovolts ($3.0 \times 10^{-12}$ V) and a quantum energy-state of picovolts. The manipulating agent may be delivered to a subject as a daily inhibitor. The method further includes determining whether the target is located within a subject; and delivering the manipulating agent to a subject as a treatment to manipulate the target, if the target is within the subject.

Disclosed herein is a system for manipulating a target, the system including a device configured to identify intrinsic parameters of the target; and a function generator adapted to generate unquantized target-tuned electrons based in part on target-tuned design factors based at least partially on the intrinsic parameters. The system includes at least one magnetic field generator adapted to prepare a container to carry the unquantized target-tuned electrons, the container being composed of superconductor quantum dots. The unquantized target-tuned electrons are transferred to the container to form target-tuned artificial atoms with quantized energy levels, the target-tuned artificial atoms acting as a manipulating agent to manipulate quantum coherence in the target. The intrinsic parameters and the target-tuned design factors are at least partially based on a mass of a mass-to-charge ratio of the target and a target-zone within the target; and the device may be a radio frequency quadrupole mass spectrometer.

Disclosed herein is a method for preparing a nanostructure for delivery to a target having quantum coherence, the method including identifying a mass from the mass-to-charge ratio of the target, via a device; and determining target-tuned design factors based at least partially on an energy-pattern based on the mass from the mass-to-charge ratio. The method includes generating unquantized target-tuned electrons fields based in part on the target-tuned design factors; and forming the nanostructure by transferring the unquantized target-tuned electrons into a container to quantize the energy levels, the nanostructure being adapted to manipulate quantum coherence in the target. Prior to forming the nanostructure, the method includes selecting the container to be composed of superconductor quantum dots. The target-tuned design factors may be based on a calibration factor, the method further including determining if a mass spectrum peak correlated to the target zone is removed or adjusted, via a validation process; and adjusting the calibration factor and repeating the validation process if the target zone mass spectrum peak is not removed or adjusted.

Disclosed herein is a method of treatment for a subject targeting a target, the method including developing a manipulating agent adapted to manipulate quantum coherence in the target. The method includes identifying intrinsic parameters of the target, via a device; and determining target-tuned design factors based at least partially on the intrinsic parameters, via a controller. The method includes generating unquantized target-tuned electrons based in part on the target-tuned design factors; and preparing a container to carry the unquantized target-tuned electrons, the container being composed of superconductor quantum dots. The method includes forming target-tuned artificial atoms by transferring the target-tuned electrons to the container, the target tuned atoms having discrete quantized energy levels; and delivering the target-tuned artificial atoms as a manipulating agent to the subject.

In some embodiments, the target is a SARS-CoV-2 virus; the target zone is the SARS-CoV-2 Nucleocapsid; the intrinsic factor is an energy pattern of about 375 volts based in part on a mass spectrometer energy of 375 kiloHertz; and the unquantized target-tuned electrons are characterized by 3.75 femtovolts ($3.75 \times 10^{-15}$ V). Delivering the manipulating agent may include applying the manipulating agent sublingually to subject. Delivering the manipulating agent may include providing the manipulating agent as a nasal spray, inhaler and/or nebulized form to the subject.

Disclosed herein is a structure including a target-tuned artificial atom including an engineered clathrate hydrate containing quantized target-tuned electrons, the engineered clathrate hydrate having a crystalline structure with a plurality of nodes. The engineered clathrate hydrate has a hollow interior portion with an inner lining of positive charges and an exterior portion at least partially lined with negative charges. The quantized target-tuned electrons are contained within the inner lining of positive charges. The engineered clathrate hydrate defines an original state with the plurality of nodes being separated by a first interatomic spacing and a compressed state with the plurality of nodes being separated by a second interatomic spacing. The second interatomic spacing is less than the first interatomic spacing. The first interatomic spacing and the second interatomic spacing may be approximately 4.68 Angstrom and approximately 3.91 Angstrom, respectively.

Disclosed herein is a method of treatment for a subject targeting a target, the method including identifying intrinsic parameters of the target, via a device; determining target-tuned design factors based at least partially on the intrinsic parameters, via a controller. The method may include generating target-tuned electrons and respective associate electric fields based in part on the target-tuned design factors; and delivering the target-tuned electrons and respective associate electric fields to the subject in order to manipulate quantum coherence in the target. In some embodiments, the target is a SARS-CoV-2 virus, the target zone is the SARS-CoV-2 Nucleocapsid, the intrinsic factor is the energy pattern of a Qsphere vector of 375 volts based on a mass spectrometer energy of 375 kiloHertz. The target-tuned electrons and fields are characterized by a quantum energy-state equal to femtovolts, a quantum work-state equal to decoherence, and a quantum energy-pattern of the Qsphere vector of 3.75 femtovolts ($3.75 \times 10^{-15}$ V).

The target-tuned artificial atoms may be delivered to the subject through dialysis. The target-tuned artificial atoms may be delivered to the subject through direct body contact. The target-tuned design factors are based on a calibration factor, the method further including determining if a mass spectrum peak correlated to the target zone is manipulated as desired, via a validation process; and adjusting the calibration factor and repeating the validation process if a target zone mass spectrum peak is not manipulated.

The above features and advantages and other features and advantages of the present disclosure are readily apparent from the following detailed description of the best modes for carrying out the disclosure when taken in connection with the accompanying drawings.

Figure 1:
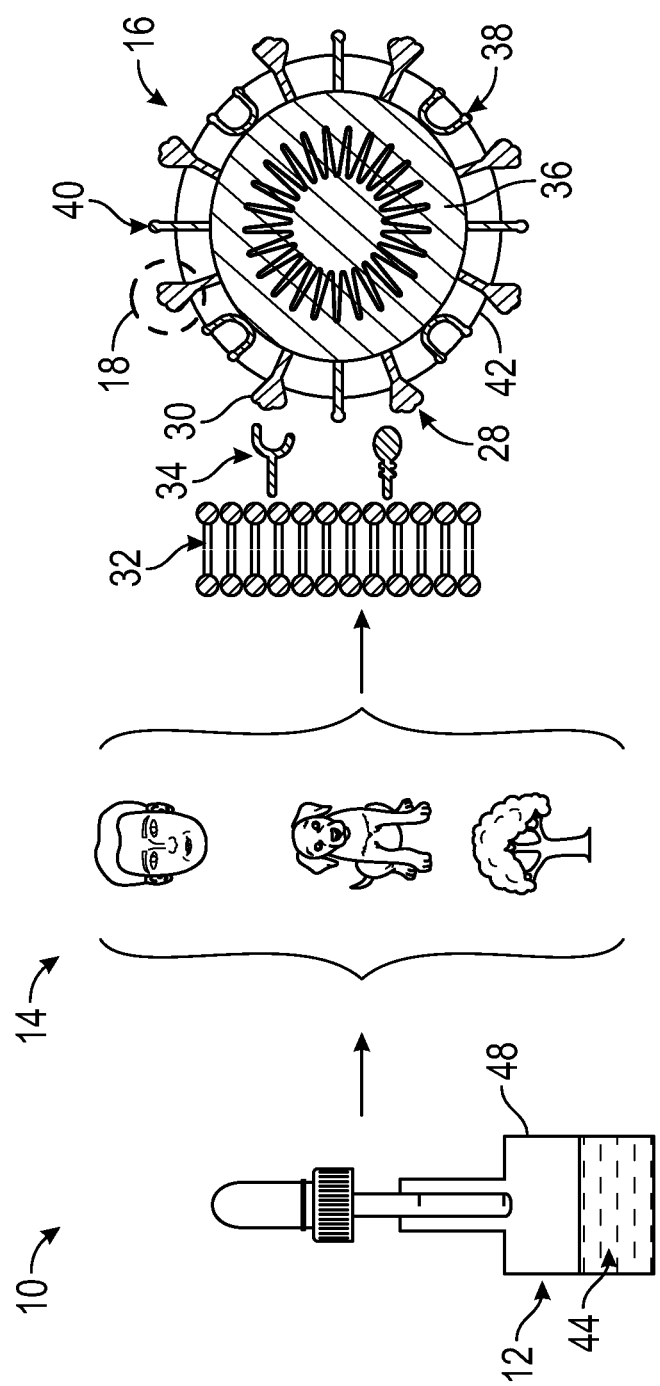
FIG. 1 is a schematic illustration of a system for manipulating the functioning of a target (which may be SARS-CoV-2 for example), the system including a controller.

The present disclosure is susceptible to modifications and alternative forms, with non-limiting representative embodiments shown by way of example in the drawings and described in detail below. Inventive aspects of this disclosure are not limited to the particular forms disclosed. Rather the present disclosure is intended to cover embodiments, equivalents, combinations, and alternatives falling within the scope of the disclosure as defined by the appended claims.

DETAILED DESCRIPTION

This disclosure addresses new and evolving areas of quantum physics, particle physics and quantum mechanics. Without intending to be limited by theory, the following description provides a narrative of the underlying theory of this new technology with a wide range of possible applications. Referring to the drawings, wherein like reference numbers refer to like components, FIG. 1 schematically illustrates a system 10 for identifying, designing, and employing a manipulating agent 12 to be delivered to a subject 14. It is understood that the drawings are intended to schematically illustrate the concept and are not to scale. The subject 14 may include but is not limited to humans; animals (including invertebrates, fish (such as farming (including salmon and tilapia), wildlife (such as trout, sharks), hobby (such as tropical)), amphibians, reptiles, birds, and mammals (such as wildlife (including buffalo and elk), agriculture (including cows, pigs, chickens), horses, dogs, cats, and rodents)); and plants (including plants and trees.) The manipulating agent 12 may be designed to manipulate the target 16 (in whole) or of a target zone 18 (in part) to affect the overall functioning of a target 16. The target 16 or target zone 18 may include any molecular system including biomolecules, macromolecules, functional groups, molecular groups that contain a molecular backbone or main chain of polymers, monomers, organelles, cells, any system that has quantum coherence (including tunneling, discordance, or entanglement) related to chemical bonds (such as covalent, hydrogen, ionic, or London dispersion forces) or internal and external cellular communication channels or bonds, or any system with a quantum beat, energy transfer, or quantum coherence (including quantum tunneling, quantum entanglement, quantum discordance, delocalized electrons, or delocalized quarks.) The molecular backbone is defined as the longest continuous chain of atoms bonded to each other that together create the continuous chain of the molecule, exclusive of all others. Biomolecules and macromolecules have a wide range of sizes, structures and functional groups and perform a vast array of functions. Like stringing together letters of the alphabet in different combinations to produce an enormous variety of words, the joining of biomolecule monomers (including sugars, amino acids, fatty acids, and nucleotides) can produce a virtually limitless collection of different macromolecule polymers (multipliers of monomers and make up much of the materials in living organisms, including proteins, cellulose and nucleic acids.)

In 1803, English physicist Thomas Young provide a demonstration to the members of the Royal Society that overturned the great Isaac Newton's ideas about the nature of light. The demonstration describes what is now known as the "double-slit experiment" to show light's wavelike nature and disputing Newton's theory that light is made of particles. He stated that it "may be repeated with great ease, wherever the sun shines." But the firth of quantum physics in the early 1900s made it clear that light is indeed made of tiny, indivisible units, or quanta, of energy, which we call photons.

At the turn of the $20^{th}$ century, the field of physics underwent two major transformations, roughly at the same time. The first was Quantum Theory and the second of Einstein's General Theory of Relativity. In 1900, physicist Max Planck presented his quantum theory to the German Physical Society. Planck had sought to discover the reason that radiation from a glowing body changes in color from red, to orange, and finally to blue as its temperature rises. He found that by assuming that energy existed in individual units in the same way matter does, rather than just as a constant electromagnetic wave—as had been formerly assumed—and was therefore quantifiable, he could find the answer to his question. The existence of these units became the first assumption of quantum theory. Subsequently, Planck found that at certain discrete temperature levels (exact multiple of a basic minimum value), energy from a glowing body will occupy different areas of the color spectrum. Planck wrote a mathematical equation involving a figure to represent these individual units of energy, which he called quantum or quanta. Planck's constant ($h=6.626070004\times10^{-34}$ $m^2$ kg/s) is the quantum of electromagnetic action that relates a photon's energy to its frequency or more generally links the amount of energy a photon carries with the frequency of its electromagnetic wave. Planck assumed there was a theory yet to emerge from the discovery of quanta, but, in fact, their very existence implied a completely new and fundamental understanding of the laws of nature. Planck won the Nobel Prize in Physics for his theory in 1918. Sixty-eight years to the day before he was born on Jun. 30, 1905, Albert Einstein theorized that not just the energy, but the radiation itself was quantized in the same manner and released the special theory of relativity. He included one of the most famous equations in mathematics, the equation—$E=mc^2$—which means "energy equals mass times the speed of light squared." It postulates that energy (E) and mass (m) are interchangeable; they are different forms of the same thing. If mass somehow totally converted into energy, it illustrates how much energy would reside inside that mass, which is quite a lot. In fact, this equation is one of the demonstrations for why an atomic bomb is so powerful once its mass is converted to an explosion. The equation also shows that mass increases with speed. In 1915 Einstein released the general theory of relativity, which is the geometric theory of gravitation and is the current description of gravitation in modern physics. The theory of general relativity has now replaced Isaac Newton's notion of simple attraction between objects with a description of matter or energy bending space and time around it, along with nearby objects following those curved paths, acting as if they were attracted to one another. It provided a unified description of gravity as a geometric property of space and time or 'four-dimensional spacetime.' In particular, the curvature of spacetime is directly related to the energy and momentum of whatever matter and radiation are present. Or, more generally gravity is the shape of space itself—it is the fabric of spacetime.

Quantum theory and Einstein's theory of relativities form the basis for modern physics. The principles of quantum physics (also referred to as quantum mechanics) are being applied to an increasing number of areas, including quantum optics, quantum chemistry, quantum computing, quantum information sciences, and quantum cryptography. Quantum applicability to biology is still heavily debated due to the quantum operating requirements which require a vacuum that provides unrestricted movement of particles and is extremely quiet to remove the effects of electromagnetic interference.

It is not coincidence that both Planck and Einstein's work forms the basis of modern physics. Planck and Einstein shared a strong relationship, with Planck being a mentor, a professional colleague, and a valued friend. Planck is also recognized for discovering Albert Einstein and his radical (at the time) theories. In 1905, Einstein lacked both a PhD and a university teaching position. Planck almost instantly supported Einstein's relativity theory, and in part through Planck's backing, Einstein became a key figure among the scientific community. Einstein's quantum father status did not come from the theories of relativity, but instead for his theory of the photoelectric effect, in which he described light as quanta. It is also interesting that two of the three quantum fathers (the other being Bohr), interestingly sought a deeper understanding of physics. It was Planck who assumed there was a theory yet to emerge from the discovery of quanta. And as many are aware of, Einstein had skepticism of the 'new physics' and titled the 1935 EPR paper (Einstein, Podolsky, and Rosen) as, "Can Quantum-Mechanical Description of Physical Reality Be Considered Complete?" This was in response to the introduction of the uncertainty principle by Werner Heisenberg, which was deemed a key piece of quantum theory with profound implications. Additionally, this may have been a rebuttal from the prestigious 1927 Solvay Conference, where German physicist Niels Bohr challenged Einstein and championed Quantum Theory. One must wonder if Bohr was just irritated after the Bohr model was discounted fourteen years prior and he sought to embrace this quantum revolution. Literature frequently states that back when Bohr was developing his model, scientists were only beginning to realize that the laws of classical physics did not apply to matter as tiny as the electron. The Bohr Model, which was presented in 1913, compared the atom to a miniature solar system. More specifically Bohr model postulates that electrons orbit the nucleus at fixed energy levels, orbits further from the nucleus exist at higher energy levels, and when electrons return to lower energy levels, they emit energy in the form of light. Many stated Bohr's model failed because it treated electrons according to the laws of classical physics and classical physics only apply to fairly large objects.

Science is interesting because it is a perpetual open book and new chapters are continually being added. As stumbling blocks are encountered between existing theories and new chapters, an opportunity is presented to stop and assess each stumbling block. Is the issue perhaps due to incorrect perceived perceptions as theories were developed? One example, with a red-blinking light, is gravity and why it still cannot be quantized. Gravity is defined as the force that attracts a body towards the center of the earth, or towards any other physical body having mass; being derived from force and acceleration being exactly equivalent to each other (measured in meters per second squared.) Or more generally, gravity is a force of attraction that exists between any two objects. There is a force of gravity between the sun and earth, between the earth and humans, and even between two marbles. The force of attraction between an object and earth is the object's weight. Gravity also determines the 'escape speed' for an object like a rocket. The stronger the gravitational pull of the object, the larger the escape speed. The introduction and evolution of gravity itself is an interesting topic. Legend has it that Sir Isaac Newton, an English mathematician, discovered gravity when he saw a falling apple while thinking about the forces of nature. Whatever really happened, Newton realized that some force must be acting on falling objects like apples otherwise they would not start moving from rest. Newton also realized that the moon would fly off away from Earth in a straight tangent line to its orbit if some force were not causing it to fall toward Earth. Newton called this force 'gravity' and determined a gravitational force exists between all objects. It was Einstein's general theory of relativity that introduced a whole new idea about gravity. According to Einstein, gravity arises from the 'warping' of space and time. Einstein's new theory of gravity explains several phenomena that would violate Newton's theory. For example, light bends when passing near massive objects like the Sun. And a clock raised above the Earth speeds up relative to a clock on the surface. However, while gravity was the first fundamental force that humanity recognized, it remains the least understood. Physicists can predict the influence gravity has on bowling balls, stars, and planets with exquisite accuracy, but no one knows how the force interacts with minute particles, or quanta. The nearly century-long search for a theory of quantum gravity—a description of how the force works for the universe's smallest pieces—is driven by the simple expectation that one gravitational rulebook should govern all galaxies, quarks, and everything in between. "If there is no theory (of quantum gravity), then the universe is just chaos. It is just random. I can't even say that it would be chaotic or random because those are actually legitimate physical processes."— Netta Engelhardt, theoretical physicist at the Massachusetts Institute of Technology. It is the theoretical physics field of quantum gravity (QG) that seeks to describe gravity according to the principles of quantum mechanics, and where quantum effects cannot be ignored, such as the vicinity of black holes or similar compact astrophysical objects where effects of gravity are strong, such as neutron stars.

When evaluating why gravity cannot be quantized, it is important to assess both quantum theory and the theories of relativity. As these equations and foundations are assessed, one thing is very evident—all are founded on time. Quantum theory links the amount of energy a photon carries with its electromagnetic wave, in which the electromagnetic wave is based on the speed of light and measured in frequency (hertz or cycles per second.) The special theory of relativity— $E=mc^2$—which means "energy equals mass times the speed of light squared." And the general relativity being a theory of space and time, with gravity being the shape of space itself—creating the very fabric of spacetime. In particular, the curvature of spacetime is directly related to the energy and momentum of whatever matter and radiation are present.

Time is interesting, to say the least. Its initial introduction into existence was casual based on humans starting to first measure and then time-box the light of the sun in years, months, days, hours, and seconds based on our artificial time measuring stick. One must note that light is more formally known as photons and photons are the force carriers (the radiation) of the electromagnetic field (measured in hertz or cycles per second.) While the speed of light had been previously measured. It was the introduction of the quantum theories of the electromagentic field that started measuring everything we know according to photons. And then with the introduction of the most famous equation in mathematics, the general theory of relativity ($E=mc^2$) pertaining to a cosmic speed limit (the speed of light) was now formally assigned to light (photons), which makes the assumption the speed of light in space really is always the same wherever it is measured from. And leads to the conclusion that energy and mass are interchangeable and that no object can travel faster than the speed of light. The concern with artificially time-boxing photons observed from Earth, photons are affected by the forces of magnetic fields—most specifically in this instance, Earth's magnetic field and defines a specific Earth vacuum. And with that—the electromagnetic field, as it has been defined, is specific to being on Earth and Earth's magnetic field and vacuum. This provides an explanation as to why spacetime fabric bends around the earth. Spacetime is the weaving of time into position to create the spacetime fabric, and photons bend with magnetic fields. If spacetime fabric bends, then the time on a clock is also going to bend. Considering the magnetic field of an object is defined by the quarks (mass) in its core, then both an object's magnetic field and vacuum is variable and specific to a given object whether a planet, star, blackhole or atom.

But the question remains on why gravity cannot be quantized. As one continues to assess all of the equations used to define gravity—knowing they all have a time or photon component—one should ask why. Photons are the force carrier of the electromagnetic field and photons have no mass. Time is based on measuring photons. The only reason light moves at the speed it does is because photons, the quantum particles that make up light, have a mass of zero. However, the foundation of gravity deals with mass and its force. Photons are not a mass field. If one is to dig deeper and look at quantum fields, dark energy, and dark mass—it is notable that standard model of particle physics and quantum field theory defines two (generalized) mass fields—electrons and quarks. So, why are we applying photons or time to gravity? At this point, a data-bias in equations needs to be considered. Data bias is defined as data that does not include variables that properly capture the phenomenon we want to predict, including data inaccurately or unknowingly produced by humans. This data may be biased against groups of things, such as for example, against photons, light, speed of light, Planck's constant, time, and the electromagnetic field. If perceptions have unknowingly driven the wrong equations and have a data-bias on items such as time, photons, and the wrong vacuum, then items such as quantum gravity start to pose seemingly big problems.

Thus, if quantized gravity is driven from a mass force then one must investigate mass fields and more specifically the dark energy and dark mass fields. The following dark energy and dark mass information was gathered from both CERN (the European Organization for Nuclear Research which operates the largest particle physics laboratory in the world) and NASA (the National Aeronautics and Space Administration responsible for the U.S. science and technology that has to do with space.) They both state that dark energy makes up approximately 68% of the universe and appears to be associated with the vacuum in space and appears to be a property of space. Because it is a property of space itself, it is distributed evenly throughout the universe, not only in space but in time. In other words, its effect is not diluted as the universe expands. The even distribution means that dark energy does not have any local gravitational effects, but rather a global effect on the universe as a whole. This leads to a repulsive force which tends to accelerate the expansion of the universe. They also state that unlike normal matter, dark matter does not interact with the electromagnetic force. This means it does not absorb, reflect, or emit light, making it extremely hard to spot. In fact, researchers have been able to infer the existence of dark matter only from the gravitational effect it seems to have on visible matter. Dark matter seems to outweigh visible matter six to one, making up about 27% of the universe. A sobering fact they present, is the matter we know and that makes up all of the stars and galaxies only accounts for 5% of the content of the universe! If a theory could provide the answers, it could help scientists gain a better understanding of the composition of our universe, in particular, how galaxies are held together. In fact, they state that galaxies in our universe seem to be achieving an impossible feat. They are rotating with such speed that the gravity generated by their observable matter could not possibly hold them together; they should have torn themselves apart long ago. The same is true for galaxies in clusters, which leads scientists to believe that something we cannot see is at work. They think something we have yet to detect directly is giving these galaxies extra mass, generating the extra gravity they need to stay intact. This strange and unknown matter is called 'dark matter' since it is not visible.

When looking to quantize gravity, it is important to note that, as previously mentioned, researchers have been able to infer the existence of dark matter only from the gravitational effect it seems to have on visible matter. They have noted that galaxies are rotating with such speed that the gravity generated by their observable matter could not possibly hold them together. If we know that mass exists in dark fields that do not obey the cosmic speed limit, then one needs to start assessing quantum field theory and string theory to find the answer. Quantum Field Theory has been speculated by many to be the jumping-off point in the effort to unify gravity and quantum theories, and especially within the string theory framework. String theory is an attempt to unite the two pillars of 20th century physics—quantum mechanics and Einstein's theory of relativity—with an overarching framework that can explain all physical reality. It tries to do so by positing that particles are actually one-dimensional, string-like entities whose vibrations determine the particles' properties, such as their mass and charge. This counterintuitive idea was first developed in the 1960s and '70s, when strings were used to model data coming out of subatomic colliders in Europe, according to a website about string theory created by the University of Oxford and the British Royal Society. Strings provided an elegant mathematical way of describing the strong force, one of the four fundamental forces in the universe, which holds together atomic nuclei. In fact, physicists have noted the different approach of string theory which swaps out particles for fiber-like strings, behave better mathematically than their point-like counterparts. This simple change has complex consequences, but one nice feature is that gravity just falls out of the math. Even if Einstein and his contemporaries had never developed general relativity, physicists would have stumbled upon it later through string theory. It has been said the underlying string unification is as simple as it is seductive. In fact, Scientists working on string theory-based analysis have established that "vibrational patterns of strings might be determined by the shape of an extra dimension and with the precise 'geometry' of the extra-dimension one could make predictions about the results of experiments one would observe."

It was Planck who originally assumed there was a theory yet to emerge from the discovery of quanta and it was Einstein who did not believe that He would roll the dice with uncertainty. As described herein, at 14.1 Angstrom, the movement of energy (electrons and quarks) exist and operate independently and in energy-states of quantum movement where they do not obey the cosmic speed limit. This phenomenon is easily realized as one assesses the impeding failure of Moore's law in computer speed after 50 years. As silicon chips have become smaller and smaller, speed has continually increased. Silicon chips have now become so small they have crept to below 14.1 Angstrom. In this dimension of quantum movement, computer (binary) bits are no longer predictable because the bits are assuming quantum movement and classical physics cannot provide the accuracy to measure quantum movement. The quantum movement below 14.1 Angstrom also underpins the Yang-Mills mass gap problem in which a positive particle (such as a quark) is traveling faster than the speed of light.

Figure 7:
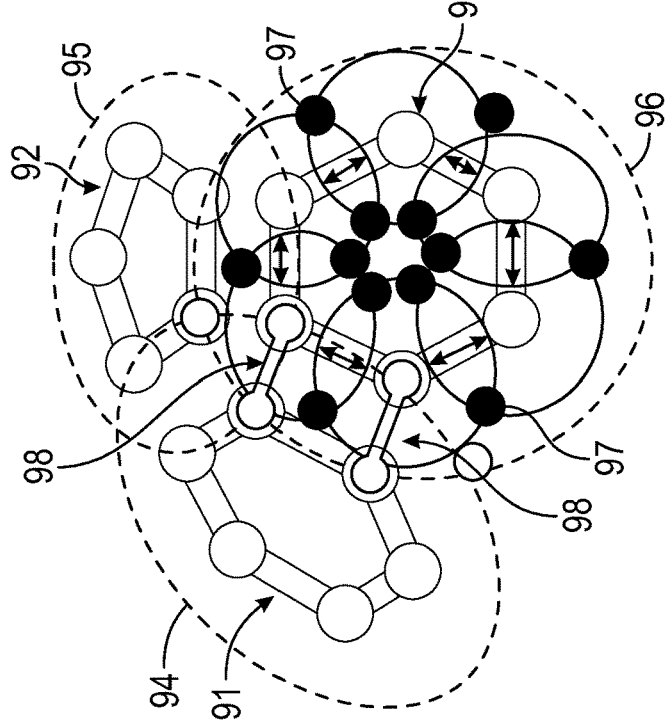
FIG. 7 is a schematic fragmentary Bloch sphere representation of radiofrequency transitions.

As described herein, the Quantum Energy Theory (hereinafter "QET") is introduced and defined as a new quantum theory. It is based on Quantum Field Theory and the dark fields of energy and mass, and particularly founded within the String Theory framework. QET defines the vibrational pattern of the string not as a vibrational pattern, but as the QET dark energy-pattern of a quantum coherent structure in which the structure is held together. This quantum coherent QET dark energy-pattern is described as the superposition of its quantum coherent states of spin, orbit, and charge. This QET dark energy-pattern also provides the one-dimensional string being defined as the total gluon force which holds the structure in quantum coherence and provides the elegant mathematical way of describing the strong force, one of the four fundamental forces in the universe, which holds together atomic nuclei. With the relationship of the quantum coherent states of spin, orbit, charge, SU(2)-SO(3) can model the mathematical relationship and this permits the use of a sphere to represent the quantum state of the quantum object such as a qubit (or a quantum energy-pattern) against the representation of a Bloch-sphere (also known to mathematicians as the Riemann sphere) or a multi-Bloch sphere which is referred to herein as a Qsphere. The geometry of the extra-dimension is then defined as a Qsphere, with a Qsphere vector being the energy-pattern of the superposition of its quantum states of spin, orbit and charge. The information of a quantum coherent system is specifically stored in the orientation of the spin and the orbit, not just the spin. The circular orbit e and the spin are locked together (like gears) due to the very strong attraction in the spin-orbit coupling (spin-orbit is also known as intrinsic spin, angular momentum, or phase.) The spin-orbit coupling is set as the energy is naturally designed (created and entangled) to form the logical structure of the structure (such as a molecule) in the femtovolt energy-state. This may have some similarities to various error correcting algorithms that re employed by DNA polymerase during replication. Energy-state is defined as the discrete energy-densities for each work-state. FIG. 7 is a schematic Bloch sphere representation of the quantum coherence manipulation within different energy-states of a Block sphere vector with radiofrequency (RF) transitions. Referring to FIG. 7, a first radiofrequency pulse rotates a pure state V into W (angle θ). The superposition state decoheres into a "ring" distribution, represented by its average, X. A second radiofrequency pulse transforms the fully decohered state X into a partially coherent state Y (angle de). The final state Z is reached only after further decoherence. Referring to FIG. 7, transfers V to W and X to Y are coherent and reversible, while transfers W→X and Y→Z are irreversible.

In addition to describing and classifying the QET dark energy-states, the ultra-microworld is formally defined as a new dimension in addition to the two existing scientific dimension references to the macroworld and microworld. This ultra-microworld contains the QET dark energy-states for the independent existence and operation of dark energy and matter. The existence of these two distinct dimensions allows dark energy-matter and visible energy-matter to exist and operate the simultaneously. QET formally defines 14.1 Angstroms (Å) as a new scientific variable that defines the split of dimensions between the ultra-microworld and the macro-microworld combination. Below 14.1 Å or 1.41 nanometers, the universe defines a split of two vastly different and particularly important worlds which can be traced to the matter-radiation decoupling point and the split of the atomic and subatomic worlds. At 14.1 Å, the earth's magnetic field no longer applies, which defines a change in the vacuum and a change in the cosmic speed limit (speed of light)—and quantum movement takes over. In this ultra-micro-world a few items are of importance: wave-particle duality does not apply because the wave (also referred to as quark or mass) and the particle (also referred to as electron or energy) are separate, meaning the electron and the atomic nucleus (quark) are not combined into an atom; without the quantized confinement or entrapment of electrons by the quarks and gluons (atomic nucleus), electrons can operate without their 'dragging' friction and confinement and now electrons do not obey the cosmic speed limit and they assume quantum movement; without the pairing of the electron (energy) and the nucleus (quarks to push the energy), the electromagnetic field does not exist, without the electromagnetic field photons (light) and phonons (sound) do not exist; which all make this ultra-micro-world extremely dark and quiet because these quantum energy-states do not interact with the electromagnetic field. The ultra-microworld being defined as the quantum behavior of dark elementary quanta (electrons and quarks) below 14.1 Angstrom. 14.1 A is defined as the start of the vacuum of space, containing the dark fields and dark energy. Dark energy and matter do not intentionally interact with the electromagnetic field. If the dark energy or matter are queried with the electromagnetic field interference is quickly introduced as things like quantum coherence fall apart. Classical quantum mechanics do not apply in the dark energy or mass including—time, speed of light, Planck's constant, electromagnetic field, light (photons), sound (phonons), Schrodinger's or any quantum principles founded on the electromagnetic field, wave-particle duality, resonant frequency, or vibrations.

The "vibrational" nature and thought currently referred to in string theory are likely a reflection of what can be witnessed within the visible matter within the electromagnetic field and below 14.1 Angstrom, but in the ultra-microworld it is energy-states that exist. The quantum coherent structure generally requires the quantum coherent sharing of atomic nuclei or quark delocalization to provide the quantum tunneling features to share the quarks of the nucleus. More generally this can be seen as the weak chemical bonds such as hydrogen-hydrogen bonds seen in solid crystals, DNA strands, and enzymes; or in artificial fashion of gases and liquids such as induced nuclear-fusion like particle acceleration to cause isotope collision or induced "spinQ-fusion" with forces (such as magnetic forces) which "re-spins the states of the energy-patterns of the electrons" to create the coherent functioning and positron pairs to create the quantum coherent structure. The quantum coherent structure requirement indeed proves that no one is rolling dice with uncertainty in this ultra-microworld. Any rolling of the dice quickly collapses, and the gluons quickly reclaim the mass and energy for redistribution into the dark energy fields.

Quantum Energy Theory further defines discrete quantum energy-states of the ultra-microworld. For the Qsphere vector, the pattern of the energy-pattern is maintained for the entire string, with increasing discrete voltage for each specific energy-state. Each energy state defines a specific work-state in the ultra-microworld. In true quantum superposition fashion, the real work states of nature and the universe are a superposition of several work-states conducted simultaneously. Currently two worlds have generally been defined, the macroworld which applies to gravity and the microworld which applies to quantum of the electromagnetic field. With the total work being done by a quantum coherent system as a quantum superposition of all work-states across the ultra-microworld, microworld, and macroworld—being conducted simultaneously. Just like a motherboard holds the brain of the computer (the CPU or central processing unit) and executes instructions usually provided by the keyboard to tell other components what to do, quantum coherent systems behave in the same fashion. The dark energy-states provide the central processing unit or brain and executes instructions usually provided by the environment (such as chemical process or brain synapses) to execute the instructions.

It is this ultra-micro dimension that allows dark quantum energy and dark quantum work to exist within the humid, wet, noisy human body—without a vacuum, without a superconductor, and without interference. It is here that the evenly distributed dark matter fields and dark energy fields of the ultra-micro-world define their requested dark matter and quanta of electrons and quarks. Because the dark energy is distributed evenly without effects of universal expansion, then the theory of relativity at $E=mc^2$ reduces to $E=m$; a theory Dirac had presented for energy and mass being interchangeable if they are borrowed and replaced in fast time frames. It is within this ultra-microworld that in-effect the quantum programming code (the dark energy-pattern) and the molecular framework code is constructed to support the physical creation of the microworld and macroworld molecular structure and radiation. It is this quantum programming code that persists and continues to run as it receives feedback from its now entangled (and coherent) microworld and macroworld, including electronic polarization, molecular (vibrational) polarization, and some orientational polarization—including particle creation, particle entanglement, structural organization, bond vibrations, side-chain rotations, loop motions, and some molecular tumbling. As the microworld and macroworld comes into existence at 14.1 Angstrom, the wave (quarks) and the particle (electron)

combine, and things are suddenly powered-up as the electrons are captured by their quarks (nucleus) and energy transfer (and life) is established. Equally as important, the electromagnetic field comes into existence, along with gravity, the speed of light, and the photons to carry the radiation of the electromagnetic field. It is these electrons and quarks that contain a superposition of energy-states from across the macro-world and micro-world (both including chemical energy and work) and the ultra-micro-world (quantum energy and quantum work) that define the total 'work' being done by a quantum coherent structure. To understand how the fabrics of these dimensions are woven together in entanglement, one can assess the energy-patterns that define this superposition.

With the definition of QET, super quantum dots (also known as artificial atoms) can be strategically designed to create target-tuned electrons to manipulate the quantum coherence of a system through its quantum work-states. The super quantum dot picking up and carrying the quantum electron energy and energy-state from the ultra-microworld and delivering it to the target in the macroworld which relocalizes the quantum electron energy and energy-state in the macro-world which collapses the DC soliton energy into electromagnetic energy for the specified target.

One analogy to assist in understanding discrete energy-states would be quantum dots. Each quantum dot, based on its size, is characterized by or holds a very specific property of emitting color of a specific bandwidth. For example, larger dots emit light that is skewed toward red, and progressively smaller dots emit light that is skewed more toward green. Quantum energy-states contain a specific density of energy to conduct quantum work. In other words, just as red Quantum Dots are distinguishable from blue Quantum Dots, femtovolt Super Quantum Dots are distinguishable from picovolt Super Quantum Dots. In one example, a properly designed femtovolt Quantum Dot may torque the quantum coherent system apart and decouple the gluons. Gluons are the force holding the system in quantum coherence. In another example, a properly designed femtovolt Super Quantum Dot may decouple and decohere the entire quantum coherent structure.

As a molecular system is decoupled with items such as femtovolt quantum energy-states, quantum coherence is lost when the gluons which are holding the coherent shell (the confinement) of the system are decoupled. The gluons are the force containing the mass and energy and define the energy-pattern properties of the coherent system. As this decoupling and decohering happens, it resembles particle annihilation—as the gluons are decoupled, the gluons (being force carriers of quarks) along with all of the mass and energy that they are containing are drawn back into the quarky core of the now non-existent quantum coherent structure—to be redistributed into the dark fields. If one were to look at a molecular system as a black hole, it seems plausible the same thing occurs. If one ventures into that system's vacuum as the decohering system collapses, all mass and energy is being drawn back in and reclaimed for redistribution, as with the bending of spacetime fabric (which contains photons) around a magnetic field (such as earth). Then, as the gluons are magnetically pulling everything into their quarky core, then it seems plausible that the spacetime fabric would also get drawn in.

In fact, it is the split of the ultra-microworld and dark matter-energy and macro-microworld visible matter-energy at 14.1 Angstroms that provides the dimension and explanation to the dark matter that is holding our galaxies together. Remember the famous equations in mathematics—$E=mc^2$—which shows that energy and mass are interchangeable and if mass somehow totally converted into energy, this would show how much energy would reside inside that mass: which would be quite a lot. This mass and energy in the dark ultra-microworld are indeed interchangeable. In fact, this not only demonstrates why an atomic bomb is so powerful—once its mass is converted to an explosion—but also the strength of the dark gluons as they present in the macroworld. It would then make sense that proposed gravitons are the equal and opposite force provided by the electrons which oppose the quarks of the atomic nucleus, and also hold the structure from collapsing in on itself. When assessing either atoms, molecules or stars—if the dark energy gluons are the 'glue' that hold the quantum coherent shell together (how an object or system is being held in angular momentum) and that quantum coherence is broken, then the gluons which are holding all the mass and energy of the vacuum are broken. In which case when gluons break it looks more like the collapse of a wave function. But the gluons are being pulled back into the quark-y core along with all the mass and energy that it contains. As they are pulled back into the core, they are distributed back into the dark energy fields for redistribution into the property of space. And if the gluons and gravitons are the dark matter-energy force, then Einstein's theory or visible matter-energy force would still hold true for the motion of bodies in a solar system.

Referring back to FIG. 1, some macromolecule examples include a target 16 or target zone 18 comprised of proteins, which have a molecular backbone of amino acids strung together with peptide bonds (used to build cells and structures, transport cells, control cell activity, maintain cell contact, signaling, catalysts and enzymes; including: enzyme proteins, structural proteins, regulatory proteins, signaling molecule proteins, defensive proteins and proteins that include unusual amino acids like canavanine); carbohydrates, which have a molecular backbone of bonded carbon, hydrogen and oxygen atoms (used for energy for cells, cell to cell communication, cell adherence, defending against invading microbes and removal of foreign material; including: monosaccharides, disaccharides, oligosaccharides, and polysaccharides); lipids which have a molecular backbone of bonded carbon, hydrogen, and oxygen atoms (used to store energy, protect layers of the skin, prevent infection and regulate cell activity and information flow in cells by altering gene expression; including: triacylglycerols (triglycerides), phospholipids, sterols and steroid hormones (such as estrogen)); nucleic acids which have a molecular backbone of nucleotides bonded together with a series of nucleotides, codons, and amino acids (used to build genetic code; including DNA and RNA and the single nucleotide of ATP (adenosine triphosphate) which is the universal battery and energy-storing molecule); and combined biomolecules, for example, a protein and carbohydrate mixed with the output of a glycoprotein (including hormones such as follicle-stimulating hormone, luteinizing hormone, thyroid-stimulating hormone, thyroid stimulating hormone, human chorionic gonadotropin, alpha-fetoprotein, and ertyropoietin (EPO)—with many of these proteins important in the development and/or detection of cancer such as prostate cancer (PSA) and ovarian cancer (CA-125)). Additionally, internal and external cellular communication channels and bonds include cell membrane receptors (including the three major classes of membrane receptors: G-Protein coupled receptors that utilize protein action, ion channel receptors that utilize ion channel opening, and enzyme linked receptors that utilize enzyme activation, such as dopamine receptors bind dopamine, insulin receptors bind insulin, nerve growth factor receptors bind nerve growth factor, ACEII receptors bind ACEII); intercellular direct signaling (including gap junctions, in which respond as a single cell and share ions); indirect signaling and travel in interstitial fluid (including paracrine signaling, in which a cell targets a neighboring cell, autocrine signaling in which a cell targets itself, and neurotransmitter signaling in which the signal is released in a synapse close to a target cell); and indirect signaling and travel in blood (including hormonal signaling in which a cell targets a distance cell through the bloodstream).

Referring to FIG. 1, the manipulating agent 12 may be designed to manipulate (such as inhibit, interfere, neutralize, edit, alter, change, restore) the target 16 or target zone 18 (including genome sequence, molecular binding, molecular bonds, affinity, binding affinity, binding shape, binding energy, bonds, bond formation, bond order, bond energy, catalyzation, chemical attraction, chemical bonds, chemical reactions, delocalized electrons, delocalized quarks, molecular backbone, functional groups, loops, energy transfer, information transfer, mass, energy, resonance frequency, communication, quantum beat, intrinsic spin, spin-orbit, angular momentum, phase, bit-flip, phase-flip, coherence time, decoherence, gluons, bosons, electrons, and quarks) of the target zone 16 (in whole) or a target zone 18 of the target 16 (in part) to affect the overall function of target 16. The system 10 can also deliver unquantized target-tuned electrons E directly to a subject 14 without the need to transfer and quantize them into an artificial atom 44 and without the need of a manipulating agent 12.

Figure 16:
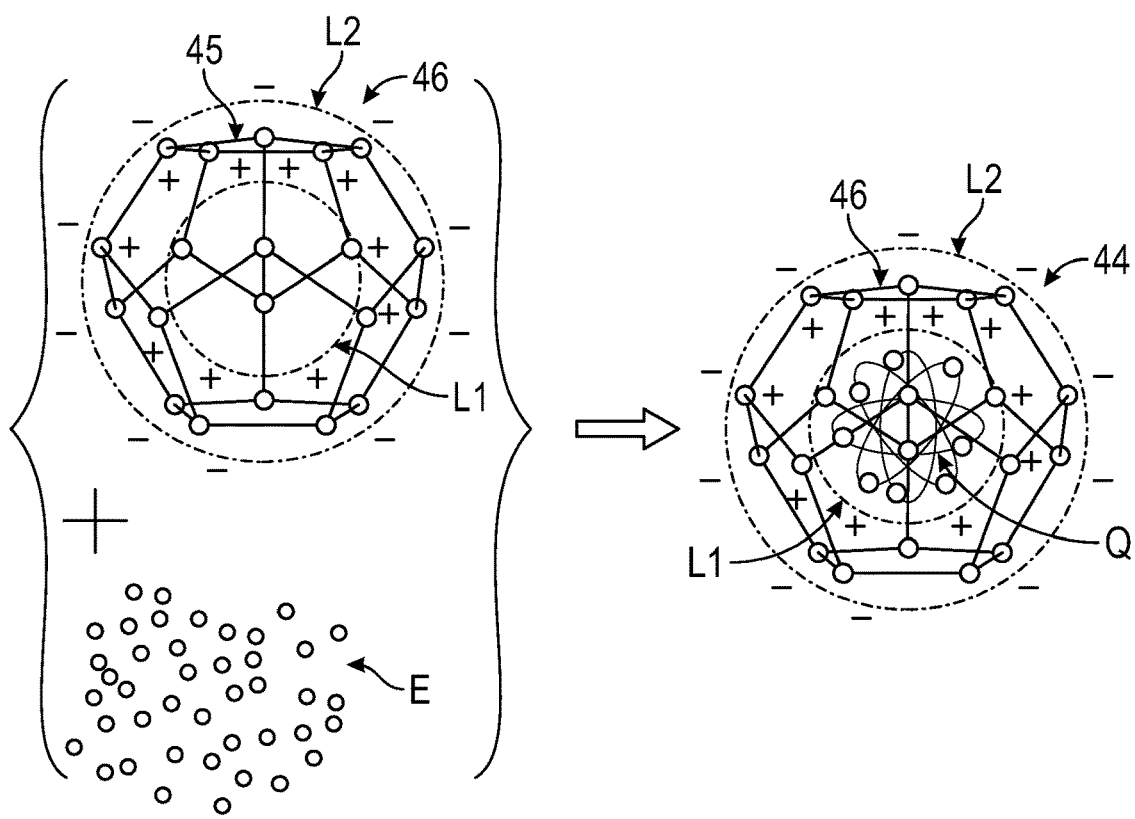
FIG. 16 is a schematic diagram showing production of a target-tuned artificial atom by combining a container and a target-tuned quantum electron field.
Figure 17:
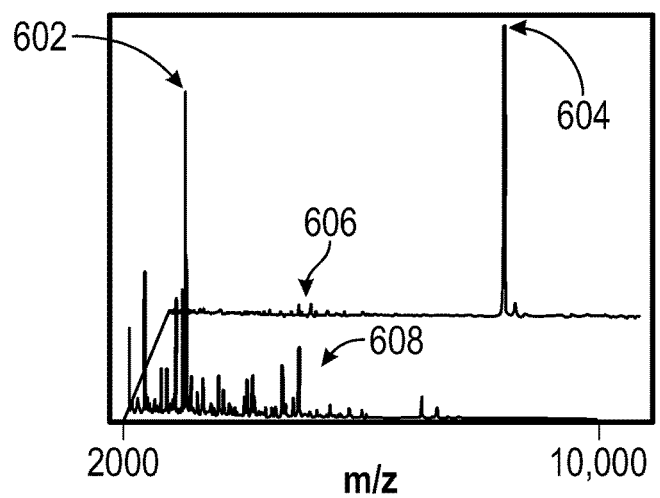
FIG. 17 is a schematic fragmentary example of a mass spectrum of a marker related to a virus.
Figure 18:
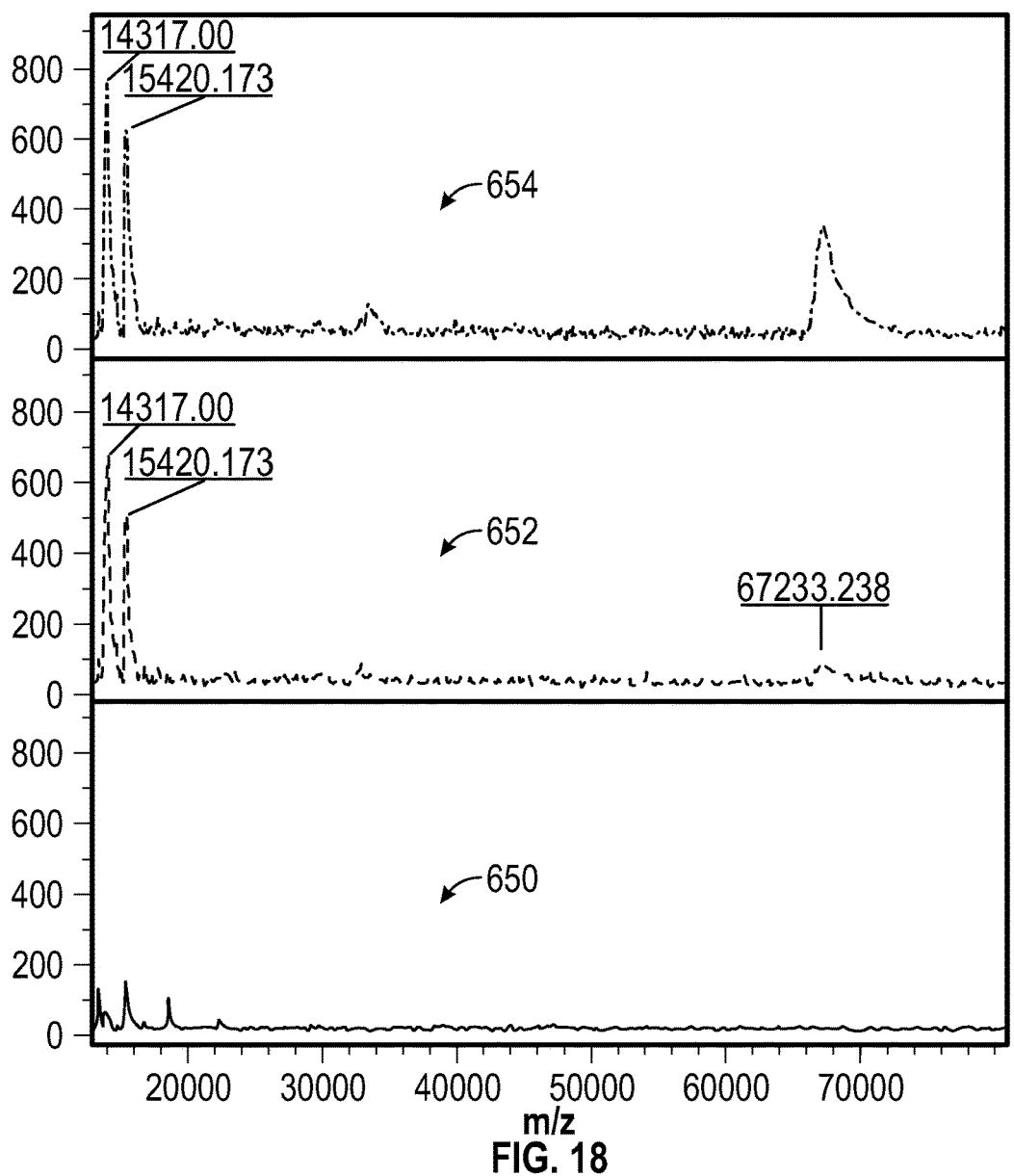
FIG. 18 is a schematic fragmentary example of a mass spectrum for a strain of influenza.

Referring to FIG. 16, the quantum energy-pattern of the unquantized target-tuned electrons E may be designed to properly manipulate the quantum coherence (including quantum tunneling, quantum entanglement, and quantum discord) of a target 16 or target zone 18 through the proper manipulation of its Qsphere vector. A Qsphere vector is used to define an energy pattern for a quantum coherent system (target 16 or target zone 18.) The energy pattern is defined as a superposition of quantum states comprised of spin, orbit and charge. Spin-orbit combined is the angular momentum (also defined as intrinsic spin, phase, gluon, coherence, or bond) and charge is electron vs positron (also referred to as matter vs. antimatter, particle vs. antiparticle.) FIG. 7 is a schematic Bloch sphere representation of radiofrequency (RF) transitions. Referring to FIG. 7, a first radiofrequency pulse rotates a pure state V into W (angle θ). The superposition state decoheres into a "ring" distribution, represented by its average, X. A second radiofrequency pulse transforms the fully decohered state X into a partially coherent state Y (angle de). The final state Z is reached only after further decoherence. Referring to FIG. 7, transfers V to W and X to Y are coherent and reversible, while transfers W→X and Y→Z are irreversible. The mathematical relationship of SU(2)-SO(3) permits the use of a sphere to represent the quantum state of the quantum object such as a qubit or an energy-pattern against the representation of a Bloch-sphere (also known to mathematicians as the Riemann sphere), or a multi-Bloch sphere which we are referring to as a Qsphere. SU(2) is the special symmetry group that describes the physics and math of a two level system which is identical to a qubit (spin ½). The spin number describes how many symmetrical facets a particle has in one full rotation; a spin of ½ means that a particle must be fully rotated twice before it has the same configuration as when it started. SO(3) in mechanics and geometry is the 3D rotation of the group, which is the group of all rotations about the origin of three-dimensional Euclidian Space R3 under the operation of composition. Its representations are important in physics, where they give rise to the elementary particles of intrinsic spin. When working with the linear representation of Lie groups and Lie algebras, it is important to keep track of the objects on which the operators act. These objects are always the elements of a vector space. In the case of O(3), the vector space is a Euclidian 3-space. For Lorentz transformations which is used for most current quantum mechanics, the vector is spacetime. However, because this is the vector representation of the ultra-micro-environment where time is not a factor the vector is based on space-energy.

A group of scientists working on string theory-based analysis established that vibrational patterns of strings may be determined by the shape of an extra dimension, and with the precise 'geometry' of the proposed extra-dimension, one could make predictions about the results of experiments one would observe. We define the energy-pattern of the quantum coherent structure as the vibrational pattern, which defines the specific geometry of energy holding a structure together. The geometry of the extra-dimension we define as the Qsphere, with its energy-pattern and vector being a superposition of its quantum states of spin, orbit and. With the discrete quantum energy-states of the energy-pattern being defined by Quantum Energy Theory; which maintains a consistent energy-pattern for the entire string, with increasing energy density for each specific energy-state. Each energy state defines a specific work-state. The total work being done by a quantum coherent system is a quantum superposition of all work-states across the ultra-micro, micro, and macro-world, which are conducted simultaneously.

Figure 2:
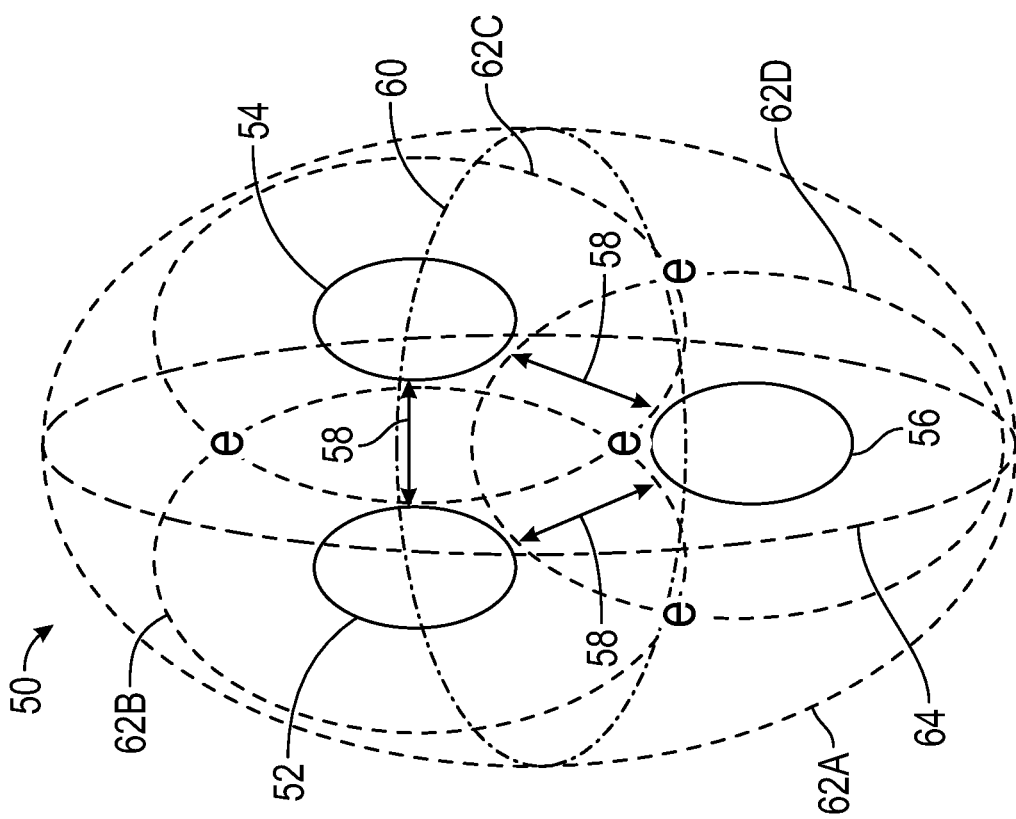
FIG. 2 is a schematic representation of a quantum coherent system.
Figure 4:
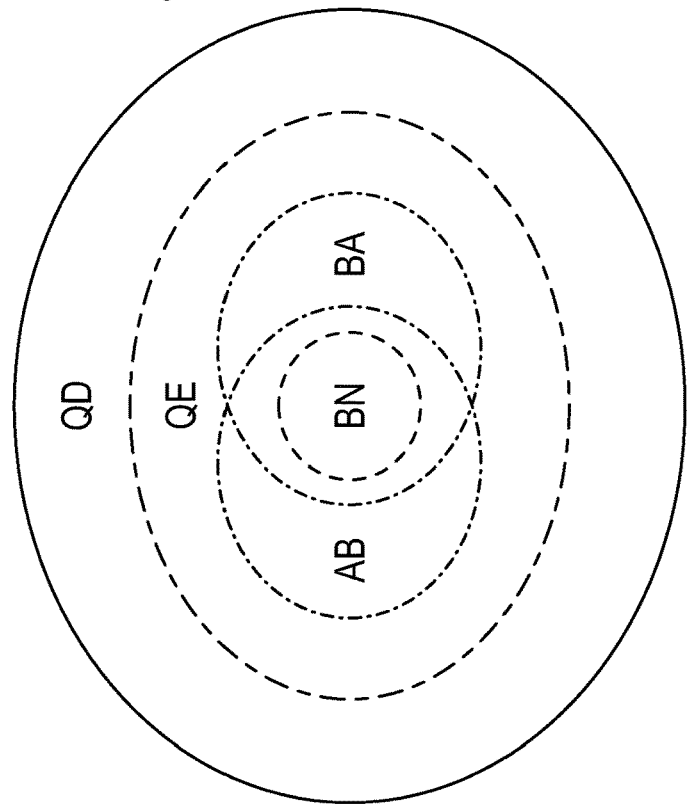
FIG. 4 is a Venn Diagram showing the relationship between quantum discord and quantum entanglement.

FIG. 2 is a schematic illustration of a quantum coherent system 50 with first, second and third atoms 52, 54 and 56 having respective covalent bonds 58 (for each pair of the atoms). FIG. 2 shows shared electrons e between first, second and third atoms 52, 54 and 56. Respective circle 60 corresponds to spin, respective circles 62A, 62B, 62C, 62D correspond to orbit and respective circle 64 corresponds to charge. As noted above, the energy pattern is a super position of spin, orbit and charge. By way of non-limiting example only as described below, 3.75 femtovolts embodies 375 volts (i.e., each is part of the same energy-pattern, just different energy-states), which also equals mass. An ion mass of target-zone (mass=375) defines the quantum coherent energy-pattern that is seen in the macroworld. This energy-pattern defines a quantum superposition of simultaneous energy-states. Many energy-states (conducting various work-activities) are required to support the quantum superposition of work, such as for example, quantum work, electrical work, and chemical work. The quantum coherent energy-pattern that we see in the macro-environment (mass=375) is a superposition of all of the work (across all energy-states), which is conducted in superposition (simultaneously). Quantum energy can be designed to manipulate the energy-pattern. In one example, a properly designed increase or reverse in the femtovolt energy-state may torque the quantum coherent system apart and decouple the gluons. Gluons are the force holding the system in quantum coherence. In another example, a properly designed change in the nanovolt energy state may change how a system is assembled. Additionally, a coherent group can be in two or more simultaneous energy-patterns which is typically referred to as quantum discord. Referring to FIG. 4, a Venn Diagram shows the relationship between quantum discord (QD), quantum entanglement (QE), Bell non-locality BN, first quantum steering (AB) and second quantum steering (BA). As understood by those skilled in the art, nonlocality describes the apparent ability of objects to carry influence or instantaneously know about each other's state, regardless of how widely spaced apart they are. Quantum steering is a special kind of nonlocal correlation that is intermediate between Bell non-locality (BN) and quantum entanglement (QE).

Figure 5:
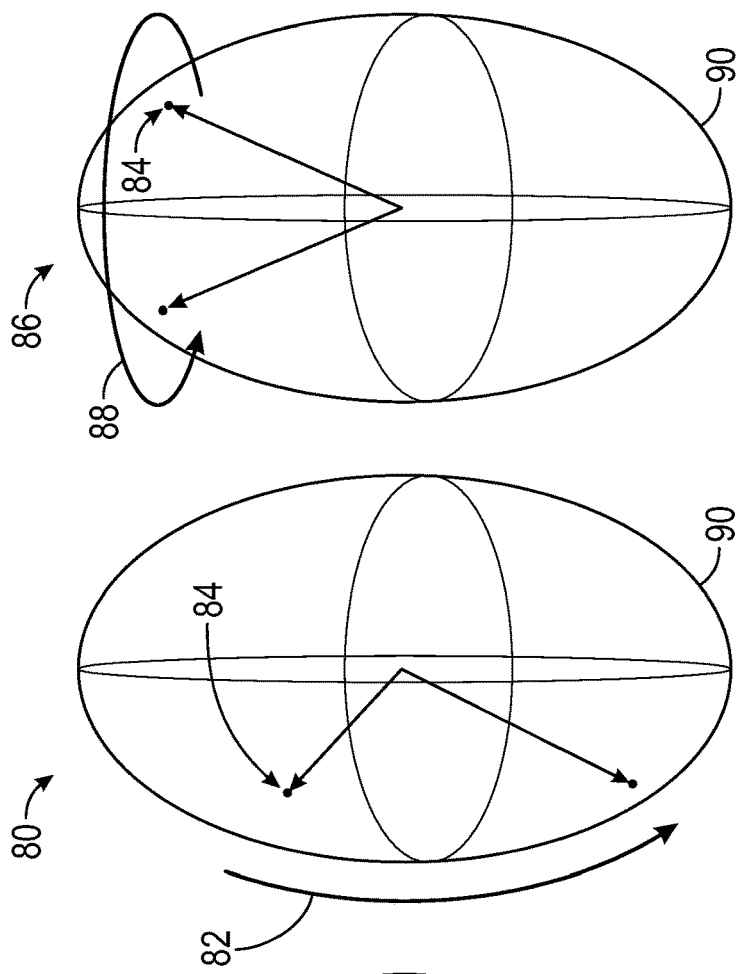
FIG. 5 is a schematic fragmentary representation of a bit-flip error and a phase-flip error in a qubit.

It is string theory that predicts every energy-pattern corresponds to a different elementary particle (such as an electron.) With the energy-pattern of an electron being defined as the energy that is holding the particle together and being the superposition of the electron's three quantum states of spin (up/down), orbit (left/right), and charge (electron/positron). Quantum coherence (quantum entanglement) is a physical phenomenon that occurs when a pair or group of particles (quanta) are generated, interact, or share spatial proximity in a way such that the quantum state of each particle (quanta) of the pair or group cannot be described independently of the state of the others. The Qsphere vector represents the coherent superposition of quantum states that lie on the surface of the sphere. In essence, we can use the same quantum error correcting algorithm that is employed by DNA Polymerase during replication. This vector can be used during the design process to determine how to design the manipulating energy-pattern of the unquantized target-tuned electrons E. With the information of an electron or coherent system being specifically stored in the orientation of the spin and the orbit, not just the spin. The circular orbit of the electron and the spin are locked together like gears due to the very strong attraction in the spin-orbit coupling (spin-orbit is also known as intrinsic spin, angular momentum, or phase.) The spin-orbit coupling is set as the electron is created as the quanta of the electron field is bundled up and entangled in the femtovolt energy-state. Energy-state is defined as the discrete energy-densities for each work-state. Work is defined as the superposition of all work-states being conducted across all energy-states, including the macro-world, micro-world, and ultra-micro-world. As coherent structures increase in size, power (magnitude) increase. The energy-pattern of the Qsphere vector must then be coupled with the proper energy-states (such as femtovolt, picovolt, or nanovolt) which takes the biophysical wave from the ultra-micro-world and quantum energy-state and relocalizes the quantum energy in the macro-dimension which collapses the DC soliton energy into electromagnetic energy for the specified target. An interference field may be introduced to cause a bit-flip (picovolts) to change the charge of an atom or phase-flip (femtovolts) to reverse or increase intrinsic spin to incite full decoherence of the coherent system by breaking the gluons which contain the coherence.) Referring to FIG. 5, a bit-flip error 80 is shown with an exchange 82 flipping a qubit 84 in latitude along a sphere 90. Also shown in FIG. 5 is a phase-flip error 86 with an exchange 88 pushing the qubit 84 halfway around the sphere 90 in longitude. The QSphere vector is defined as a multi-qubit vector as the superposition of excited states (quantum coherence) of the molecular system, which defines the energy-pattern and energy of the coherence that holds the system together. Some processes that can be leveraged for manipulation across the variety of energy-states include electronic polarization, molecular (vibrational) polarization, and some orientational polarization—including particle creation, particle entanglement, structural organization, bond vibrations, sidechain rotations, loop motions, and some molecular tumbling. In a femtovolt energy-state: energy-density affects electron creation and entanglement, allowing for decoherence. In a picovolt energy-state: energy density affects setting the charge for items such as functional group ordering and allows for bond reorganization through bond vibration, sidechain rotation, and molecular polarization. Depending on the operational intent and interpretation, whether at the subatomic level of 'particle' quantum entanglement (Copenhagen) or at the quantum field level of 'quanta' quantum coherence (Schrodinger), while differences exist, the two can be considered "operationally equivalent"—that is, equivalent for most purposes for understanding this technology. The important difference, and why this technology heavily uses and references quantum coherence, comes from the highly unleveraged quantum framework of Quantum Field Theory's ability to create, manipulate and (perceived to) destroy matter at the quantum field quanta level of electrons and quarks (the two basic matter fields.)

Because this technology heavily utilizes Quantum Field Theory, concepts are mainly explained in terms of quantum coherence but generally with the use of more commonly known subatomic particle terminology (particle, nuclear and atomic physics) such as electrons, quarks, gluons, protons, neutrons, and atomic nucleus. The additional concepts of Quantum Field Theory that are also used include the field quanta (ripples of the underlying excited fields) of the basic mass fields (including electron fields (leptons) and quarks (including up quarks and down quarks)) and the basic force fields (including gluons, bosons, photons.) Quantum coherence (quantum entanglement), namely a property of superposition of quantum states, is one of the cornerstones of quantum theory and provides significant advantages in task calculations over classical methods. Quantum coherence (quantum entanglement) is a physical phenomenon that occurs when a pair or group of particles (quanta) are generated, interact, or share spatial proximity in a way such that the quantum state of each particle (quanta) of the pair or group cannot be described independently of the state of the others. In fact, the quantum coherence phenomenon is at the existence of items such as chemical bonds, including covalent, ionic, hydrogen and London dispersion forces.

Figure 3:
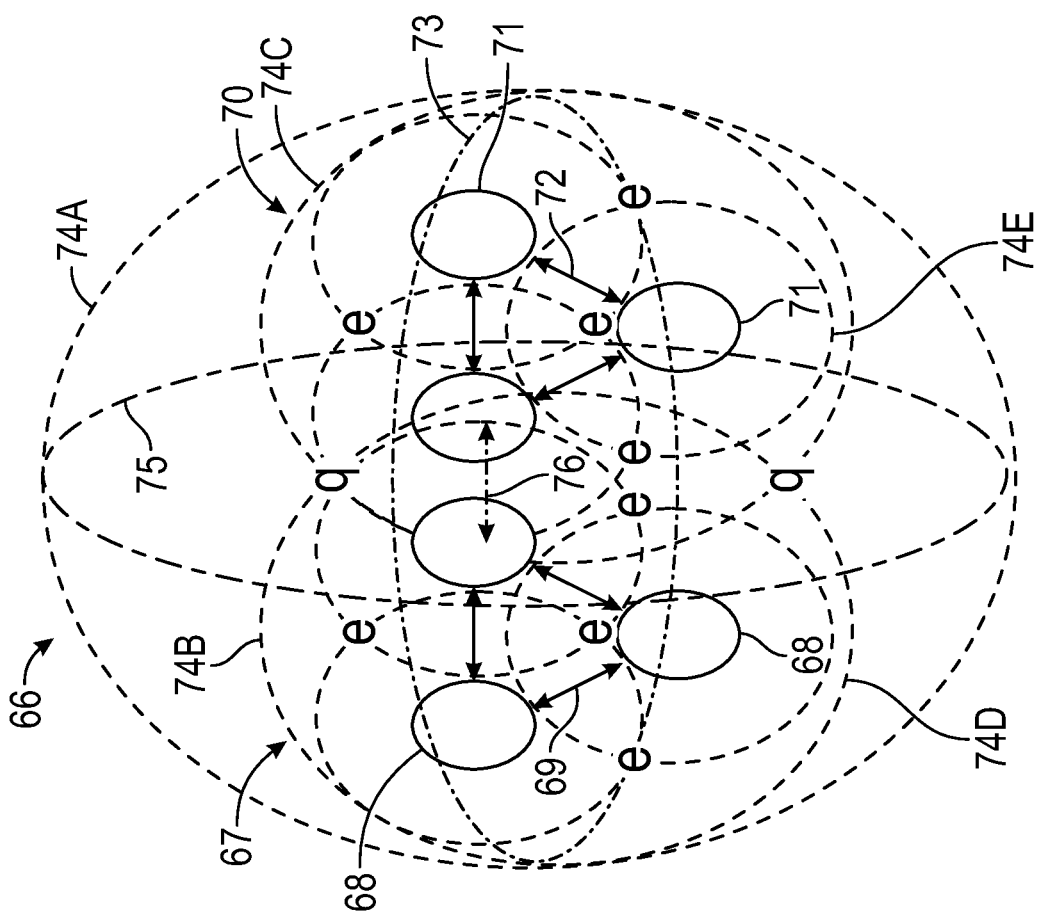
FIG. 3 is a schematic representation of a quantum discord system.

At the foundation of all biomolecules are bonds that both structurally hold them together and create the temporary connections (such as some forms of cellular communication) that are essential to life and reproduction. FIG. 3 is a schematic illustration of a quantum discord system 66 with a first quantum coherent system 67 (with a first plurality of atoms 68 having respective covalent bonds 69) and a second quantum coherent system 70 (with a second plurality of atoms 71 having respective covalent bonds 72). FIG. 3 shows the location of shared electrons e and shared quarks q. Respective circle 73 corresponds to spin, respective circles 74A, 74B, 74C, 74D, 74E correspond to orbit and respective circle 75 corresponds to charge. Additionally, there is a hydrogen bond 76 between the first quantum coherent system 67 and the second quantum coherent system 70. It is quantum functioning and quantum coherence that constructs the infrastructure to conduct these processes required for life—in one instance, the covalent bond path of a protein (the molecular backbone) is used to transfer the energy of the electrons and the hydrogen-hydrogen bonds and functional group structures of the protein are utilized to direct and move the energy. More specifically, in one instance the molecular backbone includes a pathway of covalent bonds to transfer the energy and information of the electrons (acting as 'electron' power lines); the hydrogen-hydrogen bond connections and functional groups structures, such as hydroxyl bonds, move and direct the energy and information (acting as 'quark' power poles transformers, resistors, choppers, and switches.) The resulting operation and movement of energy and information within the quantum coherent systems is termed the quantum beat. It is the heartbeat of a quantum coherent system or group of systems, such as a cell, as it moves energy in regular soliton pulses. More specifically, the quantum beat is the pulsing behavior in the intensity of radiation emitted by atomic or molecular systems that are in a superposition of excited states (quantum coherence) created by off-resonance excitation.

Figure 6:
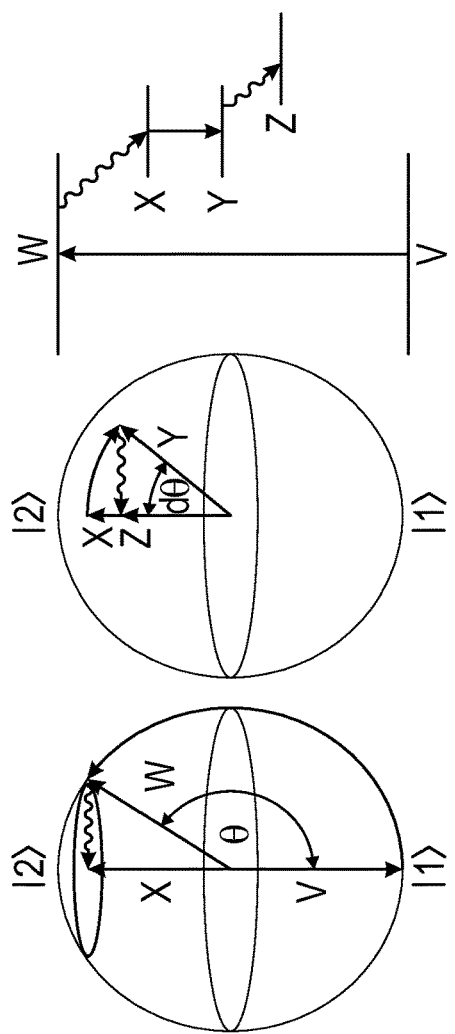
FIG. 6 is a schematic fragmentary representation of quantum discordance of multiple coherent structures in an example viral structure.

FIG. 6 is a schematic fragmentary diagram of an example viral structure with viral segments 91, 92 and 93 enclosed by respective circles 94, 95, 96. FIG. 6 illustrates the distribution of shared electrons 97 (shaded dots) and shared quarks 98 between the viral segments 91, 92 and 93. The respective circles 94, 95, 96 represent quantum discordance of multiple coherent structures, which are delocalizing the shared quarks 98 to define the gluons of the coherent shell.

All living organisms need energy to grow and reproduce, maintain their structures, and respond to their environments; metabolism is the set of processes that makes this energy available for cellular processes. Metabolism is a combination of chemical reactions that are spontaneous and release energy and chemical reactions that are non-spontaneous and require energy to proceed. However, in addition to chemical bonds there are many additional processes used by biomolecules to carry out their intended functions. Both internal and external cellular communication are essential for living organisms (surface membrane to surface membrane, exterior, and direct communication.) Internally cells need to communicate between the various biochemical steps and processes carried out within the cell. Externally cells need to communicate with other cells to coordinate activities, whether they are bacterial colonies or differentiated cells coordinating infrastructure activities within the organism. It is worth keeping in mind that communication refers to the Signal to Target to Response activities and does not imply any sort of conscious activity or understanding on the part of the participating cells. Similar in nature to a human not consciously reminding their heart to continually beat. These Signal to Target to Response processes are based on the electric (electron) and magnetic (quark) molecular makeup of their associated energy patterns. It is the signaling of the cellular communication (the electrostatic morse code of the electrons) that present the signals or requests. It is this quantum coherent foundational network of for example, the molecular backbone (electron pathway), the hydrogen-hydrogen bonds (power poles of the quarks to push energy), the functional groups structure (direct energy), and the ionic bonds and cellular communication (signaling and response) that give rise to the different energy pattern(s) and quantum beat of the system in target 16 or target zone 18, all of which can be leveraged to manipulate the functioning of the target 16. It is important to note that just because the quantum network exists, does not imply that all processes are quantum work. A vast majority of work is chemical in nature and carried out in the macro-world, which encompasses the electromagnetic field and spacetime.

However, in true quantum superposition fashion, nature's real states are a superposition of several states conducted simultaneously. Currently two worlds have generally been defined: the macroworld which applies to gravity and the microworld which applies to quantum of the electromagnetic field. To create this technology and support the scientific world, the Quantum Energy Theory is introduced in addition to the definition of a third world, the ultra-micro-world. Founded generally on Quantum Field Theory and String Theory, Quantum Energy Theory defines discrete quantum energy-states which define quantum work-states, in addition to defining a quantum energy-pattern that can be predicted in the micro-world and macro-world through mass and energy. 14.1 Angstrom is formally introduced and defined as a new scientific constant that defines the split of the ultra-micro-world. Starting at 14.1 Angstrom or 1.41 nanometers Earth's magnetic field no longer applies, which defines a change in the vacuum, a change in the cosmic speed limit (speed of light), and quantum movement takes over. This phenomenon is realized as one looks at Moore's law in computer speed, and its impeding failure after 50 years. As silicon chips have become smaller and smaller, speed has increased. They have become so small they have now crept into the ultra-micro-world and in this world of quantum movement computer (binary) bits no longer apply. In this ultra-micro-world a few items are of importance: wave-particle duality does not apply because the wave (also referred to as quark or mass) and the particle (also referred to as electron or energy) are separate, meaning the electron and the atomic nucleus (quark) are not combined into an atom; without the quantized confinement or entrapment of electrons by the quarks and gluons (atomic nucleus), electrons can operate without their 'dragging' friction and confinement and now electrons do not obey the cosmic speed limit and they assume quantum movement; without the pairing of the electron (energy) and the nucleus (quarks to push the energy), the electromagnetic field does not exist, and if the electromagnetic field doesn't exist then photons (light) do not exist; which all make this ultra-micro-world extremely dark and quiet because these energy-states do not interact with the electromagnetic field.

It is this ultra-micro-dimension that allows quantum energy and quantum work to exist within the humid, wet, noisy human body—without a vacuum, without a superconductor, and without interference. It is here that the evenly distributed dark matter fields and dark energy fields of the ultra-micro-world define their requested quanta of (dark energy) electrons and (dark matter) quarks. Because the dark matter is distributed evenly without effects of universal expansion, then the theory of relativity at $E=mc2$ reduces to $E=m$; a theory Dirac had presented for energy and mass being interchangeable if they are borrowed and replaced in fast time frames. It is within this ultra-micro-world that (in-effect) the quantum programming code (the energy-pattern) and the molecular framework code is constructed to support the physical creation of the micro-world and macro-world molecular structure and radiation. It is this quantum programming code that persists and continues to run as it receives feedback from its now entangled micro-world and macro-world, including electronic polarization, molecular (vibrational) polarization, and some orientational polarization—including particle creation, particle entanglement, structural organization, bond vibrations, sidechain rotations, loop motions, and some molecular tumbling. As the micro-world and macro-world comes into existence at 14.1 Angstrom, the wave (quarks) and the particle (electron) combine, and things are suddenly powered-up as the electrons are captured by their quarks (nucleus) and energy transfer (and life) is established. Equally as important, the electromagnetic field comes into existence, along with gravity, the speed of light, and the photons to carry the radiation of the electromagnetic field. It is these electrons and quarks that contain a superposition of energy-states from across the macro-world and micro-world (both including chemical energy and work) and the ultra-micro-world (quantum energy and quantum work) that define the total 'work' being done by a quantum coherent structure. To understand how the fabrics of these dimensions are woven together in entanglement, one can assess the energy-patterns that define this superposition. A good analogy to discrete quantum energy-states are quantum dots. Each quantum dot, based on its size holds a very specific property to emit a color of a specific bandwidth: larger dots emit light that is skewed toward red, and progressively smaller dots emit light that is skewed more toward green. Quantum energy-states contain a specific density of energy to conduct quantum work.

The sophisticated, energy-consuming process and tendencies of cellular protein folding provides a good example of a quantum coherent energy-pattern that contains the superposition of energy-states across the ultra-micro-world, micro-world, and macro-world.

In one example, the target zone 18 is the functional group hydroxyl covalent bonds (O—H) of the molecular backbone of the SARS-CoV-2 Spike Protein. The hydroxyl bond quantum work-states include the charge being set and continuing to function in the picovolt quantum energy-state. With a picovolt energy-state interference, the hydroxyl bond orders are reversed (OH to HO) and the Spike-Protein structure folds incorrectly to produce the incorrect protein folded shape. With the incorrect shape, the S-Protein cannot dock into the cell receptor and reproduce. In another example, the target zone 18 is the molecular backbone and covalent bonds of the nucleocapsid of the SARS-CoV-2 N Protein. The molecular backbone and covalent bonds quantum work-states include the logical order and entanglement that are set and continue to function in the femtovolt energy-state.

Protein folding, a molecular origami if you will, depends on the way amino acids are strung, twisted, and held together with covalent bonds, to fold into a myriad number of complex three-dimensional shapes. It is these shapes that give proteins their unique powers over the environment and determine their functionality. The result of the three-dimensional structure of the protein holds a great deal of biological importance. The final structure of the cellular protein exposes several channels, receptors, and binding sites, and affects how it interacts with other proteins and molecules. For example, a protein fold of a certain shape may function as an enzyme, while a protein fold of another shape may function as an insulin molecule. In fact, it is widely known that rogue misfolded proteins can cause a vast array of diseases. Additionally, the accumulation of misfolded proteins is now understood to play a major role not only in cancer, but in dementia and other chronic diseases as well. Protein folding is comprised of four levels of folding, including primary structure, secondary structure, tertiary structure and quaternary structure. The first two levels of protein folding are conducted within the ultra-micro-world. The primary structure folding and functioning exists at the quantum femtovolt energy-state and the quantum work-states includes electron creation (setting the logical structure of the molecule structure) and entanglement (setting the intrinsic spin.) The secondary structure folding, which in this example are the hydroxyl bonds of the molecular backbone, exists and functions at the quantum picovolt energy-state and the quantum-work includes setting the charge for the functional group attachment order (through processes such as bond vibration, side chain rotation and quantum tunneling). With the molecular system (backbone, hydrogen bonds and functional groups) of the protein set up, the last two protein folding levels (the tertiary structure and quaternary structure) are carried out in the micro-world and macro-world. Once the protein structure is ‘turned on’, that is once the micro-world and macro-world is added into the superposition of total work and the electrons are captured by the nucleus, the quarks power everything up and the protein structure snaps into place based on the molecular configurations that have been put into place. Energy transfer and the quantum beat of a quantum coherent molecular system is established.

The system 10 can be designed through the ultra-micro-world including electronic polarization, molecular (vibrational) polarization, and some orientational polarization—including particle creation, particle entanglement, structural organization, bond vibrations, sidechain rotations, loop motions, and some molecular tumbling. For example, the femtovolt energy-state defines the quantum work-state where electrons (mass) are created and entangled; and appropriately, when viewing electron functioning within femtosecond spectroscopy, one will find bonds appearing and disappearing as electrons are created and disappear as they look for entanglement to maintain their existence (quantum coherence). To create matter to either ‘remove’ a bond or entanglement or prevent phase-flips (such as molecule quantum coherence or quantum computing), the use of the femtovolt quantum energy-state can introduce an electron (femtovolt) to manage or manipulate a quantum coherent relationship. In quantum computing, the femtovolt energy-state and work-state interference can be viewed as the introduction of phase-flips—where it breaks the gluons of quantum decoherence and the energy and mass (quanta) are drawn back into the quarks and the field flattens. This is viewed as the disappearance of entanglement and electrons. The picovolt energy-state defines quantum work-states such as quantum tunneling and their electron (dipole) swapping and vibrations as items such as functional bonds (including hydroxyl bonds) set the correct ‘bits.’ To ‘rearrange’ the order of how bonds are formed or to manipulate or manage bit-flips (such as in molecule quantum coherence or quantum computing), use the picovolts energy state. In quantum computing, the picovolt energy-state interference may be viewed as the introduction of bit-flips, in which interference is introduced, and must be corrected since it is viewed as the ‘wrong answer.’ Similarly, there are additional energy-states including nanovolts and additional process including electronic polarization, molecular (vibrational) polarization, and some orientational polarization—including particle creation, particle entanglement, structural organization, bond vibrations, sidechain rotations, loop motions, and some molecular tumbling and protein folding that use a variety of quantum processes quantum coherence, quantum tunneling, quantum entanglement and quantum discord and non-quantum processes such as simple chemical reactions.

The system 10 may be employed for the identification (such as in serum or in sample), diagnosis, monitoring, personalization, prevention (such as inhibition), mitigation, and treatment (such as neutralization or repair) of a vast array of pathogens (such as known or existing, new, novel, antibiotic resistant, or mutation), diseases, illnesses, infections, and conditions (such as malaise, abnormal conditions or symptoms)—including acute (such as acute viral or allergen responses); chronic (such as autoimmune, pathogen, or disease); and root cause (such as genetic and epigenetic mutations, immune system dysfunctions, health dysfunctions, physiological factors, chronic pathogens, trauma or injury, structure (muscles, bones, fascia), quantum biophysics (transfer of electrons between FE-S molecules, energy pattern balance), biochemistry (including everything produced by the body, everything consumed (including food and liquid), environmental exposures (including air and toxins) and emotional biomarkers (including chemical bio signals, hormones, heart rate, oxygen saturation)). A list of potential applications may include pathogens, such as viruses (including Ebola, HIV, EBV, Herpes, and Hepatitis), bacteria, parasites, fungi and protozoans (including African Sleeping Sickness, amoebic dysentery, and malaria); mutating pathogens (including HIV-1, which has the highest reported mutation rate for any biological entity at 4.1+−1.7× 10E-3 per base cell); antimicrobial resistant pathogens (including the CDC urgent threats of carbapenem-resistant acinetobacter, candida auris, clostridioides difficile, carbapenem-resistant Enterobacteriaceae, drug-resistant neisseria gonorrhoea); fast acting pathogens (including GAS (group A streptococcal disease of necrotizing fasciitis) and *Naegleria fowleri* (the brain eating amoeba)); pathogen networks (including biofilms); antigens (including toxins such as pseudomonas exotoxin (PE), diphtheria toxin (DT) or ribosome-inactivating proteins (RIPs) and allergens); immune system dysfunctions (including autoantibodies, bone marrow damage and vascular damage); genetic and epigenetic dysfunctions, such as DNA SNPs, CNVs, and mutations (including Hereditary Spinal Paraparesis or intronic SNP in DNA mismatch repair gene PMS2 (r51059060, Ser775Asn) associated with increased sperm DNA damage and risk of male infertility, RNA such as ribosomes (including 30s subunits of ribosomopathies of ribosomal component proteins or rRNA genes including those of cancer and inherited bone marrow failures); biomolecule dysfunctions such as protein dysfunctions of proteopathies (including neurodegenerative diseases from misfolds, aggregates and toxic proteins found Alzheimer's and Parkinson's and prior diseases such as such as chronic wasting and mad cow disease); rogue protein molecules (including multiple sclerosis (MS), frontotemporal dementia (FTD), or Amyotrophic lateral sclerosis (ALS)); rare protein dysfunctions (including diseases such as porphyria which has 150 people reported in the world); cell communication dysfunctions (gap junction and nerve injury such as neuropathy, nerve entrapment, compressed nerves, or entrapment); and other entities.

In one example, the target 16 is a SARS-CoV-2 virus. SARS-CoV-2 is an icosahedral, enveloped, beta coronavirus with a single-stranded RNA genome, like MERS-CoV and SARS-CoV. The genome size is approximately 26-32 kilobases. The first two-thirds of the viral 30 kb RNA genome, mainly named as ORF1a/b region, translates into two polyproteins (pp1a and pp1ab) and encodes most of the non-structural proteins (NSP). The remaining parts of the virus genome encode accessory proteins and four essential structural proteins, including spike (S) glycoprotein, small envelope (E) protein, matrix (M) protein, and nucleocapsid (N) protein. The first target zone 18 of interest is the SARS-CoV-2 biomolecule structure of the spike (S) glycoprotein 30 which is required for viral binding and viral replication and an area that many vaccine developers target. In SARS-CoV-2 the spike (S) glycoprotein is highly conserved among all human coronaviruses (HCoVs) and is involved in receptor recognition, viral attachment, and it is the sole viral membrane protein responsible for Subject 14 (host) cell entry.

The second target zone 18 of interest is the SARS-CoV-2 biomolecule structure of the nucleocapsid (N) protein 36 in which the viral capsid often plays a critical role for both viral structure and viral function and makes them an area of great pharmacological interest. In coronaviruses (including SARS-CoV-2), the nucleocapsid (N) protein alone can form the capsid, it is a multifunctional RNA-binding protein necessary for viral RNA transcription and replication. With the capsid protein building blocks arranged according to well-defined geometric relationships, capsid morphology can be governed by: icosahedral (e.g., HBV, poliovirus), helical (e.g., Ebola) symmetry rules, conical, polymorphic structure that lacks overall symmetry (e.g., HIV-1). Capsids are finely tuned, robust biomolecular devices and although their morphology and biological functions can vary markedly, complete viral capsid (sometimes referred to as the shell) are required for both structure and function.

The manipulating agent 12 may be employed or delivered through artificial atoms 44 or for some applications (such as cutaneous nerve injury to incite quantum coherence or tumor to incite quantum decoherence) as unquantized target-tuned electrons E through direct contact transfer (such as a contact patch, inflatable band, band or cuff, wand, or wearable device) from a device or function generator 52. The artificial atom 44 of the manipulating agent 12 is not susceptible to enzymatic degradation, stomach acid, or the first pass of the liver. Efficacy is driven by bioavailability and bioavailability is driven from particle (molecular) size and kinetic solubility which make the manipulating agent 12 effective for a variety of delivery methods. The manipulating agent 12 may include a variety of delivery methods and routes that may be adapted to carry or hold a given quantity of the manipulating agent 12 in liquid form, including taken by mouth (orally); given by injection into a vein (intravenously, IV), into a muscle (intramuscular, IM), into the space around the spinal cord (intrathecally), or beneath the skin (subcutaneously, sc); placed under the tongue (sublingually); inserted into the rectum (rectally) or vagina (vaginally); placed in the eye (ocular route) or the ear (otic route); sprayed into the nose and absorbed through the nasal membrane (nasally); breathed into the lungs, usually through the mouth (inhalation) or mouth and nose (nebulization); applied to the skin through an open wound or cut (cutaneous) for a local (topical) effect; delivered to a wound through a patch (transdermal) for a local (topical) effect; or applied directly with a machine such as dialysis.

Referring to FIG. 1, the target 16 may be a virus. In some embodiments the manipulating agent 12 is designed to work as short-term, protein targeted, neutralizing artificial antibodies to neutralize an active viral infection within the subject 14. In other embodiments the manipulating agent 12 adapted to act as short-term, protein targeted, inhibiting artificial antibodies to both upregulate the immune system and prevent or reduce a viral infection within the subject 14. In some embodiments, referring to FIG. 1, the target 16 may be a virus with a target zone 18 having at least one viral ligand-receptor structure 28, such as the spike protein ligand 30 (or S protein) that acts as a deception molecule to deceive a host cell receptor 34. The spike protein 30 may dock into the receptor 34 of a host cell 32 of the subject 14 and inject viral genome for viral replication. Referring to FIG. 1, the target zone 18 may include a membrane protein 38, envelope protein 40, a lipid membrane 42 or other zones.

In one embodiment, the target 16 is the SARS-CoV-2 virus that is denaturing the ACEII cellular receptor. In another embodiment, direct communication between cells is important and the target 16 is an entrapped nerve in which the gap junctions have lost quantum coherence. Gap junctions are the only intercellular channels in humans and animals that allow the direct exchange of ions and small signaling and metabolic molecules between neighboring cells and have crucial roles in many biological processes, including development, tissue, and organ synchronization, and immune response. Gap junctions are water-filled physical channels that allow small signaling molecules, called intracellular mediators, to diffuse between the two cells. The transfer of signaling molecules transmits the current state of one cell to its neighbor. This allows a group of cells to coordinate their response to a signal that only one of them may have received. In plants, there are plasmodesmata between almost all cells, making the entire plant into one giant network.

In another embodiment, some diseases are caused by the disorders of membrane receptor function due to deficiency or degradation of the receptor via changes in the genes that encode and regulate the receptor protein and the target 16 is a genetic mutation. Gap junctions are unique intercellular channels formed by the proper docking of two hemichannels from adjacent cells. One cited gap junction study comes from mutations in the genes encoding gap junction subunits, connexins (Cxs), which have been associated with several inherited human diseases, such as peripheral neurogenerative disease, central hypomyelination, non-syndromic hearing loss, cataracts, skin diseases and developmental abnormalities. Based on the crystal structure of the Cx26 gap junction, a homology model was developed that predicted six hydrogen bonds at the docking interface; in mutations most of the hydrogen bonds were predicted to be lost.

In addition to chemical bonds, many additional processes are used to carry out required functions including internal and external cellular communication which are essential for living organisms. In another embodiment, the target 16 or target zone 18 is a molecule, virus, mutation or injury or illness causing loss of quantum coherence that is denaturing, blocking or causing dysfunction in either internal or external cellular communication. Cells must respond to changes in their immediate environment including receiving and process signals that originate outside their borders. Diseases typically present when these communication channels, receptors or signaling are blocked, denatured or built incorrectly. Understanding the characteristics of the communication channels is important in understanding how to design a manipulating agent 14. Some target 16 or target zone 18 examples are molecules or injury causing cellular communication problems, including: misfolded proteins or biomimicry structures that block or denature the communication or channels; genetic mutations or SNPs which may cause a cell membrane receptor to be built incorrectly and therefore functioning incorrectly; injured cells may be targeted for rebuilding to restore structure, signaling, and communication (such as entrapped nerves); or the overload of signaling molecules (if causing damage or problems) due to a blocked receptor.

In another embodiment, the manipulating agent 12 is the direct contact and delivery of the electrons and fields to a target zone to restore or incite quantum coherence of the water within a subject 14. The identification of the target zone 18 may be through testing methods such as quantitative phase imagining (QPI) to assess cell biology such as cell fragmentation and water loss for necrosis and aptosis; long term maintenance of osmotic balance; metabolism of the organelle level; macromolecular crowding; and intracellular water gradients during cell chemotaxis. Much of water's value for molecular biology comes from both the structural and dynamic characteristics of its status as a complex, structured liquid as well as its nature as a polar, protic (hydrogen atom bound to an oxygen, a nitrogen, or a fluoride and readily donates protons to solutes), and amphoteric (agent and base) reagent. Both intercellular and intracellular water are intriguing subjects. A substantial fraction of intracellular water forms a tight hydration shell around cytosolic proteins and does not participate in osmotic balance. This osmotically inactive (OI) water makes up as much as 20-60% of the entire water. The OI volume appears to be a dynamic quantity that varies with physiological state of the cell. Transitions between OA and OI water have been implicated in cancer as well as normal metabolism. The importance of OI water is underscored, by the remarkable observation that, in some cells, 50% of intracellular water can be of metabolic, and not environmental origin. Due to the properties of water clusters and "water ordering" around a hydrophobic particle in which the structure provides the crystal or lattice structure with Hydrogen-Hydrogen bonds and the particle provides the stability for the maintained structure and acts as one of the key driving forces for protein folding and the formation of functional multiprotein aggregates. It also sustains the self-assembly of lipid membranes and matching of hydrophobic surfaces often observed in protein-ligand binding. Hydrophobic interactions are a dominant force in molecular biology and mimic the more common small water clusters. Small water molecule clusters constantly activate human cells and carry more minerals and oxygen to cells. [Reference: The significance of cell water content in cell biology. Michael Model, Dept of Biological Sciences, Kent State University. Researchgate.net]

The manipulating agent 12 includes quantized target-tuned electrons Q that are engineered to manipulate all or a portion of the target 16. Target-tuned refers to designing target-tuned factors per FIG. 9 (Block 104). The intrinsic and design-factors include calculating the energy-pattern, energy-states, QSphere vector and designing the appropriate interference field to assign to the electron E energy-pattern and energy-state for a target zone 18 within a specific target 16. Engineered refers to deliberately bundling unquantized target-tuned electrons E or energy (creation of matter-antimatter or electron-positron) by explicitly exciting the quantum electron field. The target 16 is the overall molecular structure, while the targeted zone 18 is a specific molecular structure within the target 16.

Figure 9:
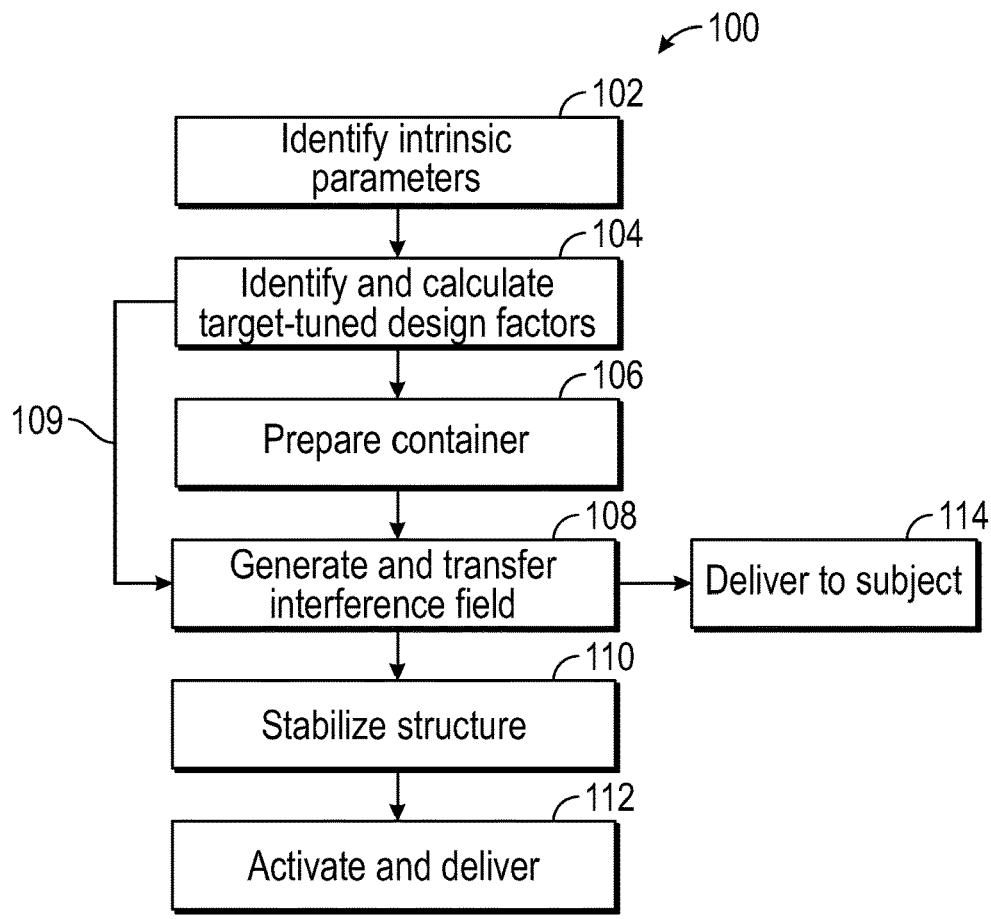
FIG. 9 is a schematic flowchart for a method executable by the system of FIGS. 1 and 2.

Referring to FIGS. 1 and 16, the quantized target-tuned electrons Q are carried by target-tuned artificial atoms 44 that are delivered through a carrier, container or containing structure, referred to herein as "container 46." Referring to FIG. 16, once a first vibration is applied the target-tuned artificial atoms 44 are formed when the quantized target-tuned electrons Q (as defined by the quanta of the underlying quantum electron fields) are transferred into a container 46 (described below with respect to blocks 106, 108 and 110 of FIG. 9). Referring to FIG. 16, the container 46 is composed of a crystalline structure 45 having an inner lining L1 and an outer lining L2. The inner lining L1 is composed of positive charges (e.g. positrons) and the outer lining L2 is composed of negative charges (e.g. electrons). The left side of FIG. 16 shows unquantized target-tuned electrons U having respective associated electron fields. The left side of FIG. 16 shows electrons are 'quantized' (contained by a positive charge), referred to herein as quantized target-tuned electrons U (having respective associated electron fields) and are now artificial atoms 44. The quantum coherent collective functioning of the positrons and electrons created from the Meissner effect suspends the now quantized target-tuned electrons Q in three dimensions within the positive inner lining L1 and repels the magnetic and electromagnetic fields out with the negative outer lining L2, allowing energy to flow undisturbed and without resistance.

Artificial atoms are the name given to certain man-made nanostructures that (only) emulate the behavior of a real atom, in the sense of discrete energy levels. However, artificial atoms give engineers and scientists the flexibility to design custom energy levels with the artificial atom charge and with the energy being quantized like an atom. When electrons are confined to a small space and are trapped by a positive charge (such as the nucleus of an atom, the gates of a quantum dot or the positive interior lining of the artificial atom) which confines their movement in three dimensions, they are forced into discrete quantum states, these electrons behave differently as compared to their counterparts in free space with their behavior only explained by quantum mechanics. The confined electrons produce a quantum electron waveform structure, which is mechanically analogous to an atom. The electrons within artificial atoms may orbit around a center much like a traditional atom, however its center is distinguishable by the lack of a nucleus, most notably the magnetic quarks that comprise the proton.

The unquantized target-tuned electrons E are transformed into quantized target-tuned electrons Q, (with discrete charge and energy levels), as part of the target-tuned artificial atoms 44. The target-tuned artificial atoms 44 manipulate the quantum coherence of the specific target zone 18 in the target 16. The quantized work done through the target-tuned artificial atoms 44 being completed by transporting the target-tuned quantum energy-states out of the ultra-micro-world (dark world) and into the macro world and collapsing the quantum biophysical soliton voltage into the electromagnetic field (also referred to as relocalization) to affect quantum work-states. This process creates and then transports the quantum (dark) energy from the ultra-micro-world (below 14.1 Angstrom) to the macro-world of greater than 14.1Angstrom without loss of energy or interference from electromagnetic field. With the transportation of the dark energy into the macro world, the work conducted is not electromagnetic (chemical or radiation), but quantum physical in nature by decoupling the quantum coherence (decouples the gluons) holding the electron shells together which is neither endothermic nor exothermic. Both endothermic and exothermic result from conducting work in micro-world and macro-world, resulting in chemical/radiation work within the electromagnetic field. With the decoupling of the quantum coherence, the mass and energy of the structure get pulled back into the quarks to return to the dark fields for redistribution.

The manipulating agent 12 may be comprised of the target-tuned artificial atoms 44 (which includes the quantized target-tuned electrons Q contained in a container 46). Alternatively, the manipulating agent 12 may comprise the quantum electron field E delivered directly to the subject 14, without a container 46. The formation process of the target-tuned artificial atoms 44 (also referred to as super quantum dots) is a multi-step process that requires creating the container 46 (such as engineered, tunable clathrate structure 400) within a solution of distilled water through inducing quantum coherence through electromagnetic induction and then inducting the solution with the target-tuned electrons E. The container 46 is paired with the quantized target-tuned electrons Q through a first vibration. Additionally, an electromagnetic induction is applied to stabilize and compress the energy within the target-tuned artificial atoms 44.

Figure 8:
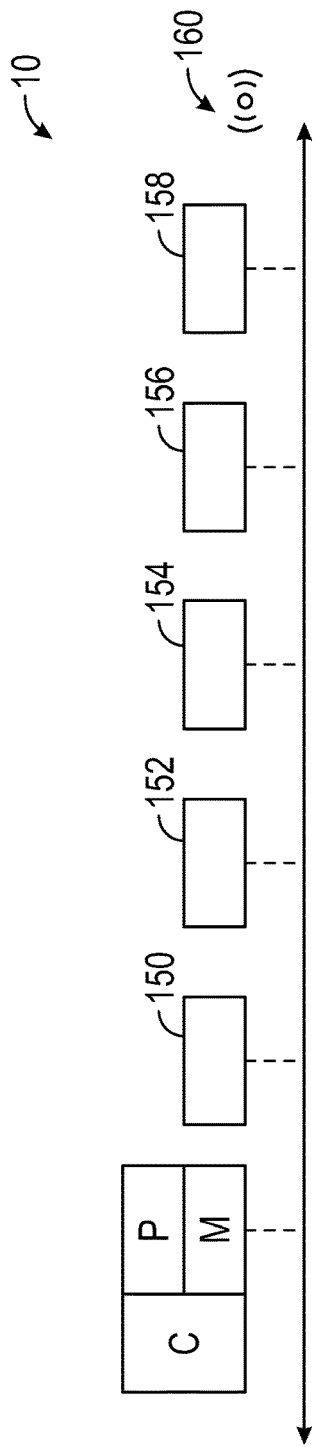
FIG. 8 is a schematic block diagram of various components of the system of FIG. 1.

Referring now to FIG. 8, a schematic block diagram of various components of the system 10 is shown. FIG. 9 is a flow chart of a method 100 for manipulating the target 16. Referring to FIG. 8, the system 10 includes a controller C having at least one processor P and at least one non-transitory, tangible memory M on which instructions are recorded. The memory M can store controller-executable instruction sets, and the processor P can execute the controller-executable instruction sets stored in the memory M. The method 100 may be at least partially executable by the controller C of FIG. 8. Referring to FIGS. 1 and 8, the system 10 may include a function generator 152 (which may be DC powered) adapted to generate the unquantized target-tuned electrons E. The system 10 may include at least one magnetic field generator 154 adapted to prepare the container 46 to carry the target-tuned electrons F.

Figure 10:
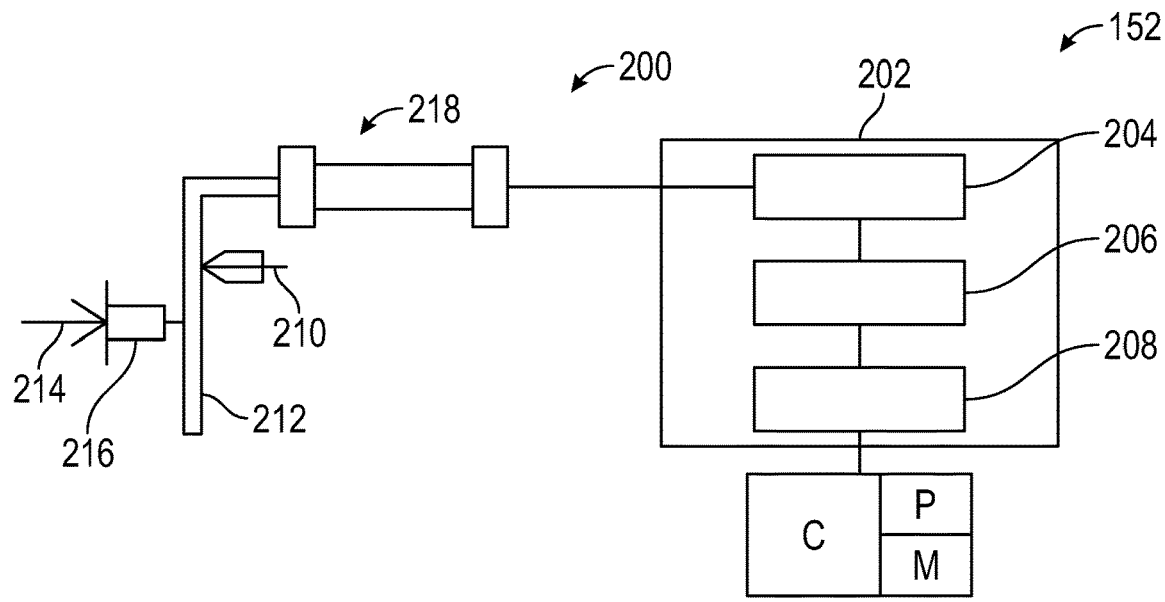
FIG. 10 is a schematic diagram of a set-up employable by the system of FIGS. 1 and 2, the set-up having a mass spectrometer.

Referring now to FIG. 9, method 100 need not be applied in the specific order recited herein, i.e., the order may be changed. It is also understood that some blocks may be omitted. Per block 102 and block 104 of FIG. 9, the method 100 includes identifying intrinsic parameters of the target 16 and further target-tuned design factors of the target 16 (in whole) or target zone 18 (in part), which may be identified via a device 150 (see FIG. 8). Referring to FIG. 10, an example of a first set-up 200 is shown for obtaining the intrinsic parameters of the target 16 and target-tuned design factors of the target zone 18. In this example, the intrinsic parameters include an energy-pattern and QSphere Vector calculated from the mass spectrum peak of the target 16 and a target-tuned design factor is the mass spectrum peak of a target zone 18 and the device 150 is a mass spectrometer 202. The mass spectrometer 202 is adapted to measure masses and relative concentrations of atoms and molecules. The mass spectrometer 202 includes an ion source 204, a mass analyzer 206 and a detector 208. It is to be understood that the device 150 may take alternative forms and include additional components and circuitry not discussed herein.

Referring to FIG. 10, a sample 210 containing the target 16 or the target zone 18 is injected into a tube 212. A high-pressure solvent 214 may be injected into the tube 212 via a pump 216. The sample 210 and the solvent 214 pass through a liquid chromatography column 218 filled with a solid adsorbent material. Each component in the sample 210 interacts slightly differently with the adsorbent material liquid chromatography column 218, resulting in different flow rates for the different components and leading to the separation of the components as they flow out of the liquid chromatography column 218 and are subsequently processed through the mass spectrometer 202. Referring to FIG. 10, the data from the mass spectrometer 202 may be employed by the controller C to obtain the intrinsic parameter and the target-tuned design factors. As noted above, the controller C has at least one processor P and at least one non-transitory, tangible memory M on which instructions may be recorded.

Figure 11:
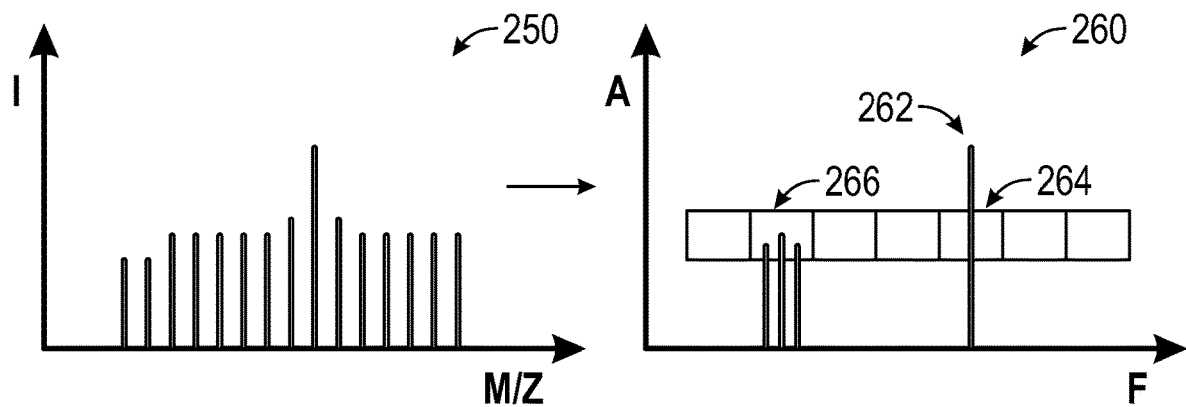
FIG. 11 shows a schematic example of a mass spectrum produced by the mass spectrometer of FIG. 10 and a Fourier transform of the mass spectrum.

Referring to FIG. 11, an example of a mass spectrum 250 is shown, with the ion signal intensity on the vertical axis and the mass-to-charge ratio m/z on the horizontal axis. The peaks obtained on the mass spectrum 250 may be compared to a baseline control mass spectrum for identification. The baseline control mass spectrum may be obtained, for example, through databases of known mass spectrum data and peaks available to those skilled in the art. In order to isolate the mass spectrum peak for a specific target 16, a validated control sample may be used as a "baseline" to compare with positive samples, for the purpose of identifying aberrant peaks between the mass spectrum. The positive samples are samples that have been deemed as positive samples for the target 16 in question. Alternatively, the sample 208 may be subject to a general assessment to identify potential targets and identify potential cofactors in a condition, to identify novel targets, to identify target mutations, or target mutations that may have multiple aberrant peaks. In another embodiment, where the targeted zone 16 is a ligand to a subject 14 (host) cell receptor, such as the viral (biomimicry) ligand of SARS-CoV-2 (S) Protein and subject 14 (host) cell receptors of ACE2 or Band 3, the RRM model may be used to identify appropriate cell receptors for ligand match, analyze known cell receptors for match potential, or to cross-validate designs and options for the affinity (interaction) and phase applicability between the ligand and the cell receptor(s) to couple with other technology such as mass spectrometry. The RRM model uses a transformation of amino acid sequences to spectral densities based upon the de-localized electron densities along the biomolecule backbone (also known as the resonant energy transfer in the distribution of free electron energy along the biomolecule backbone) along with the associated radians for the ligand-receptor pair. The Resonant Recognition Model (RRM) is a biophysical model that analyzes proteins and their DNA or RNA targets. The RRM is founded on the notion that all proteins can be considered as linear sequences of their constitutive elements (amino acids). The RRM model interprets this linear information using signal analysis methods including spectral and space-frequency analysis. It has been found that the spectrum of the distribution of the energies of free electrons along the proteins is critical for protein's function (interaction). As there is evidence that certain charge could travel along the proteins then charge moving through the protein backbone and passing different energy stages caused by different amino acid side groups can produce sufficient conditions for the specific electromagnetic radiation or absorption. These results lead to the conclusion that specificity of protein interactions are based on the resonant electromagnetic energy transfer between interacting molecules with a specific frequency for each observed function/interaction. An algorithm incorporating the Resonant Recognition Model available to those skilled in the art may be employed. This may be done by comparing RRM cross-spectra function of ACE2 receptors and spike proteins from SARS-Cov-2, See https://www.mdpi.com/2076-3417/10/11/4053/htm. Other methods may include identifying, analyzing or cross-validating results, studies, or values of the SARS-CoV-2 (S) Protein affinity against antiviral or pharmaceutical products. using native state electrospray ionization mass spectrometry (See https://www.nature.com/articles/s41401-020-0483-6 #Tab2).

Figure 19:
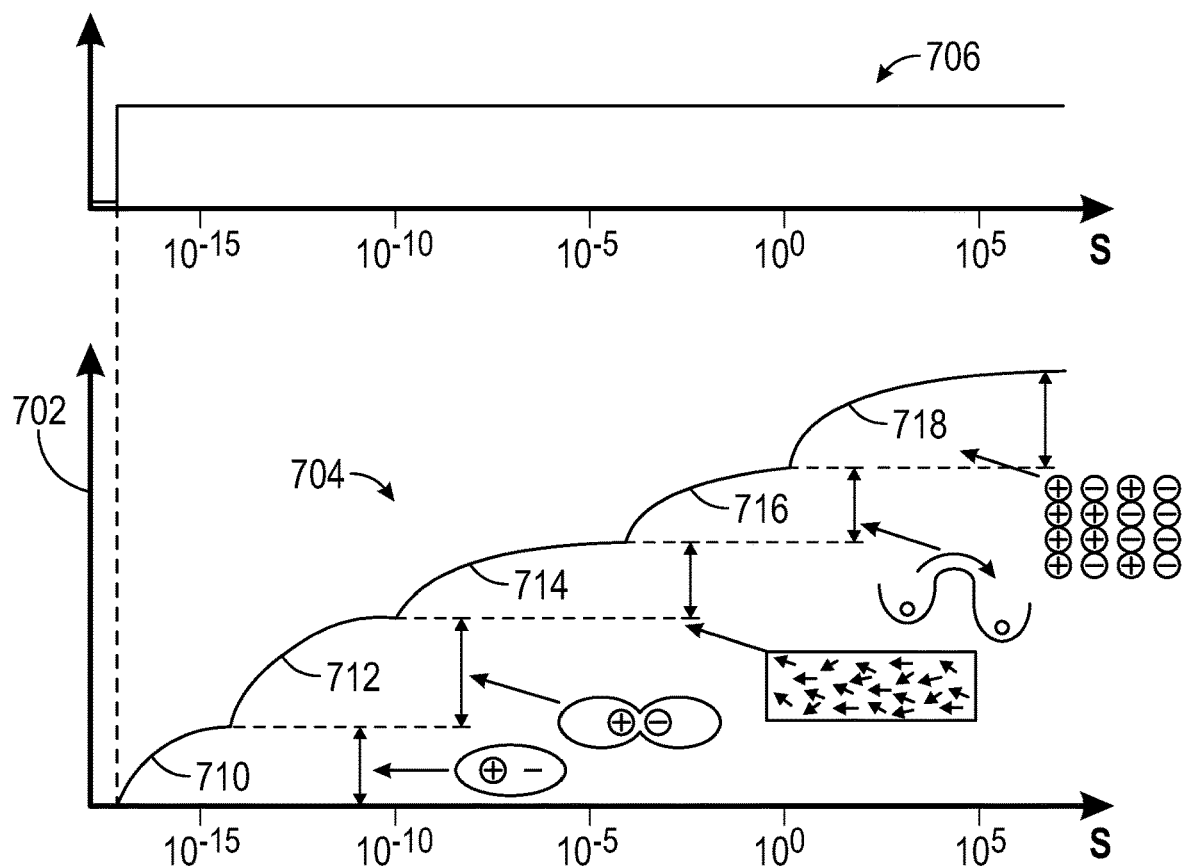
FIG. 19 is a schematic graph illustrating polarization on the vertical axis and time on the horizontal axis.
Figure 20:
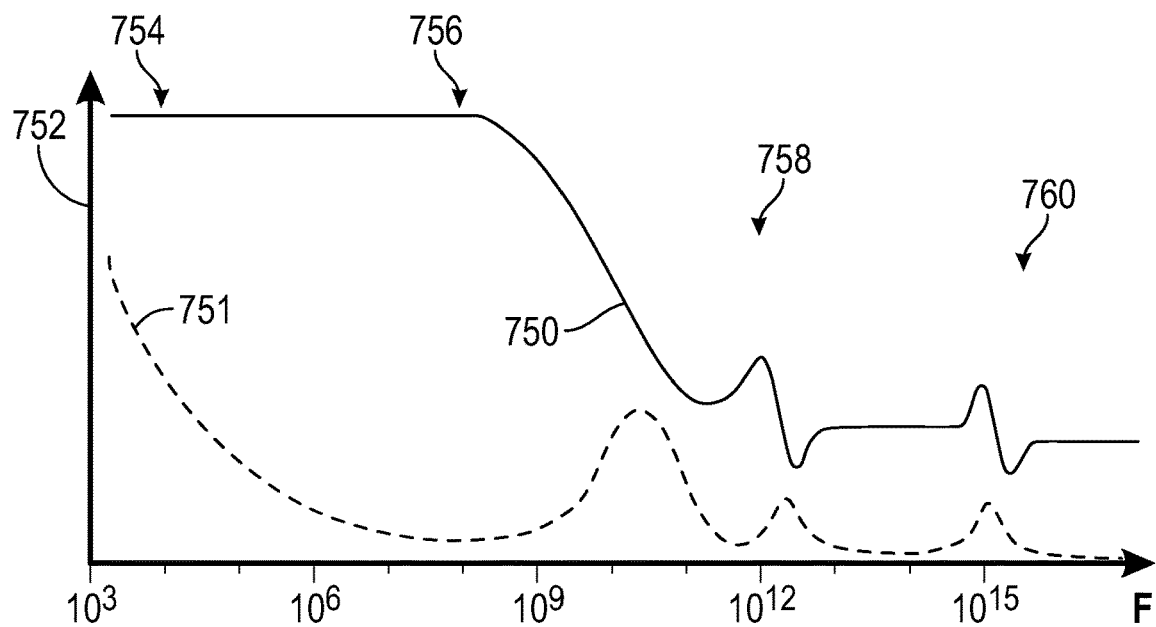
FIG. 20 is a schematic graph illustrating energy amplitude on the vertical axis and frequency on the horizontal axis.

Other methods for analyzing the interaction (affinity) may include Nuclear Magnetic Resonance (NMR) to collect protein structural data by inducing a magnetic field through samples of concentrated protein. Depending on the chemical environment, a sample will absorb specific radio frequencies. Protein nuclear magnetic resonance may be applied to study intermediate structures in time scales of picoseconds to seconds since protein structural changes operate on this time scale. Referring to FIG. 19, the vertical axis 702 shows polarization, while the horizontal axis shows timescale in seconds (S). Trace 704 shows induced polarization in response to an applied electric field 706. Portion 710 of trace 706 corresponds to electronic polarization, portion 712 corresponds to molecular polarization, portion 714 corresponds to orientational polarization, portion 716 corresponds to hopping polarization and portion 718 corresponds to a space charge polarization. Other methods may include running additional peptide assays or genetic sequencing to assess and analyze the sequence structure during design or testing. An inverse timescale is shown in FIG. 20. Traces 750 and 751 illustrate the types of energy absorbed in various parts of the spectrum by a sample. The vertical axis 752 shows amplitude and the horizontal axis shows frequency F (in Hertz). The first region 754 corresponds to ionic energy, the second region 756 corresponds to dipolar energy, the third region 758 corresponds to vibrational energy and the fourth region 760 corresponds to electronic energy.

Figure 12:
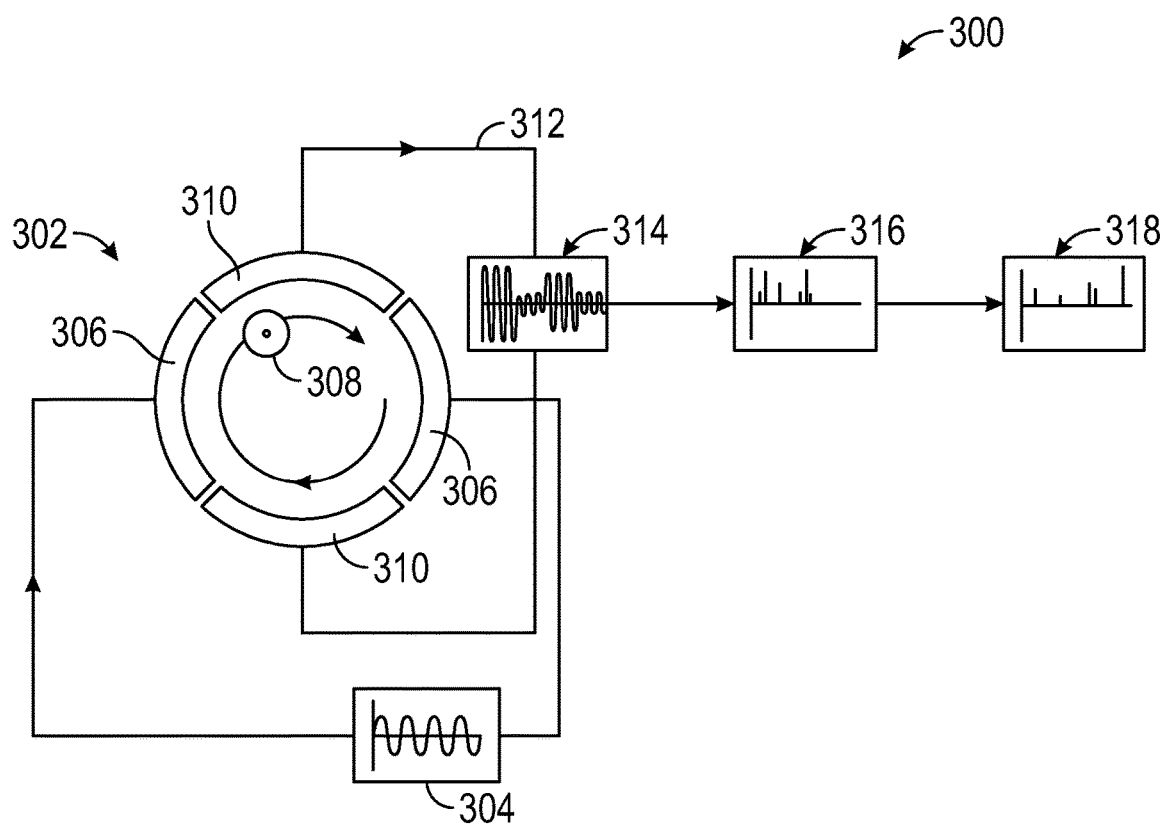
FIG. 12 is a schematic diagram of an alternative set-up employable by the system of FIGS. 1 and 8, the set-up having a mass spectrometer that utilizes radio frequency signals.

Referring now to FIG. 12, a set-up 300 is shown for obtaining the intrinsic parameters of the target 16 and the target-tuned design factors of the target zone 18. Here the intrinsic parameters and target-tuned design factors of the energy-pattern which defines the QSphere vector are the mass (mass-to-charge ratio of the mass-domain) or the energy (frequency of the frequency-domain from a radio frequency (RF)) of the quadrupole mass spectrometer 302. Quadrupole mass analyzers use oscillating electrical fields to selectively stabilize or destabilize the paths of ions passing through a radio frequency (RF) using the resonance excitation method to determine at what point ions are ejected. The RF quadrupole mass spectrometer 302 may be an Orbitrap Fusion Lumos Tribrid mass spectrometer, for example. Referring to FIG. 12, an oscillating RF electric field is generated by source 304 and directed towards excitation plates 306. This causes trapped ions 308 to oscillate back and forth in the harmonic axial potential and induce a current that is detected by electrodes 310. The induced current (indicated by line 312) is encoded in the form of a time-domain spectrum 314. The time-domain spectrum 314 is converted to a frequency-domain spectrum 316 (which is then converted to a mass spectrum 318 after mass correction). Since each distinct m/z value has a distinct axial frequency, the frequency-domain spectrum 316 here is in effect a relative mass spectrum 318. The mass spectrum may have a peak at m/z of 375 which, when the charge z is equal to 1, this then becomes the mass of the electrons (ions) and is in the macro-world energy-state of volts which equates to the work-state of intracellular energy transfer. This also equates to a frequency domain mass spectrum peak of 375 kHz which defines the bond ejection resonance in the radio frequency spectrum which is in the macro-world of kilovolts energy-state and equates to the cell bond ejection work-state. Either the mass (m/z of mass-domain) or energy (the m/z of the frequency (in Hertz) of the frequency-domain may be used as the intrinsic parameters for the energy-pattern for the QSphere vector for target 16 in identifying the target or the target-tuned design factors of target zone 18 in designing the solution of the manipulating agent 12.

Per block 104 of FIG. 9, the method 100 includes determining target-tuned design factors for the target zone 18 based at least partially on the intrinsic parameters (determined in block 102) of the target 16. Referring to FIG. 1, the target 16 may be a virus. In some embodiments the manipulating agent 12 is designed to work as short-term, protein targeted, neutralizing artificial antibodies to neutralize an active viral infection within the subject 14. The target-tuned design factors in this embodiment might include intrinsic factors of the target such as: (1) Target: SARS-CoV-2; (2) Target Energy-Pattern: Mass of 375 at a Work-State of Cell Coherence and intracellular energy transfer, the Energy-State being in Volts; and (3) Type: Active Viral Infection. Additionally, the target-tuned design factors may include: (4) Design Description: short-term, protein targeted, neutralizing artificial antibodies to neutralize an active viral infection; (5) Target Zone: SARS-CoV-2 Nucleocapsid (N) Protein 36 (viral capsid or nucleocapsid protein); and (6) Target Zone Reason: The (N) protein of the viral capsid is a highly immunogenic and an abundantly expressed protein during infection. Viral capsids (sometimes referred to as the shell) are of great pharmacological interest due to their often-critical role in regulating viral infection pathways and essential component in the viral life cycle regarding their structural and functional roles in housing, protecting, and ultimately delivering the viral genome (RNA or DNA) needed for viral replication. They are finely tuned, robust biomolecular devices and although their morphology and biological functions can vary markedly, complete viral capsid (sometimes referred to as the shell) are required for both structure and function.

The target-tuned design factors may further include: (7) Target Zone Intent (e.g., neutralize and kill the virus/target 16; (8) Energy-State: Femtovolts: Phase-Flip with Work-State: (e.g., incite decoherence in the quantum coherence of the capsid protein bonds); (9) the Qsphere Vector being a Target Zone Mass of about 375 m/z, with the Energy-State being in Volts, the Work-State being Cell Coherence (e.g., via an Orbitrap Mass Spectrometer). When the charge z is equal to 1, then 375 factor (m/z) becomes the mass of the electrons (ions). Alternately, the Qsphere Vector may be equivalent to the target zone energy. The mass spectrum frequency domain can also be used in another embodiment with an intrinsic factor of 375 m/z (with 375 kHz at an Energy-State of Coherence Bond Ejection Resonance) determined via Orbitrap Mass Spec. This is the energy required to break the coherent structure apart through the use of frequency. Additional target-tuned design factors include: (10) Target Zone Energy-Pattern: Energy-State being 375 volts at the Work-State of Cell Coherence and intracellular energy transfer; and (11) Manipulating Electrons Energy at 3.75 femtovolts.

In other embodiments the manipulating agent 12 adapted to act as short-term, protein targeted, inhibiting artificial antibodies to both upregulate the immune system and prevent or reduce a viral infection within the subject 14. The target-tuned design factors in this embodiment may include intrinsic factors of Target: (1) Target: SARS-CoV-2 (2) Target Energy-Pattern being 375 at an Energy-State of Volts and Work-State of Cell Coherence and Intracellular Energy Transfer; and (3) Type: Prevent Viral Infection and Upregulate Immunity. The factors may include design factors such as: (4) Design Description: Short-term, protein targeted, inhibiting artificial antibodies to both upregulate the immune system and prevent or reduce a viral infection; (5) Target Zone 18: SARS-CoV-2 Spike (S) Protein 34; and (6) Target Zone. These are useful because he spike (S) glycoprotein 30 which is required for viral binding (docking) and viral replication is an area that many vaccine developers target. In SARS-CoV-2 the spike (S) glycoprotein is highly conserved among all human coronaviruses (HCoVs) and is involved in receptor recognition, viral attachment, and it is the sole viral membrane protein responsible for entry into a cell of the subject 14 (host). Additional target-tuned design factors include: (7) Target Zone Intent: Manipulate Bond Order Protein Assembly Process (e.g., for target zone 18). The intent is to manipulate the bond order to change the protein shape. With a change in shape, the virus cannot dock and replicate in the cellular membrane. Thereby allowing the subject 14 to identify the virus and naturally create the required antibodies in the absence of an infection. Additional target-tuned design factors include: (8) Energy-State: Picovolts and Work-State=Bit-Flip, Change Hydroxyl Bond Order to manipulate protein shape; (9) Target Zone Qsphere Vector and Energy-Pattern being. 312 Molecular Resonance at an Energy-State of Microvolts, the Work-State being Molecular Bond Coherence via RRM (electromagnetic Frequency being 10E13, Terahertz); and (10) Manipulating Electrons Energy at 30 picovolts.

In some embodiments, the target 16 (or target zone 18) is selected to be the ACE2 autoantibodies. Depending on the intent, there are different ways this may be designed. ACE2 autoantibodies may be technically defined as the 'IgM autoantibodies that recognize ACE2 (angiotensin converting enzyme-2).' Per some studies, ACE2 autoantibodies have been found in 18/66 (27%) patients with severe COVID-19, which are rare (2/52; 3.8%) in hospitalized patients who are not ventilated. Additionally, autoantibodies to ACE2 may be associated with constrictive vasculopathies. (https://pubmed.ncbi.nlm.nih.gov/33083808/). Neutralizing antibodies may also show effects of antibody-dependent enhancement (ADE) and amplify disease progression. The system 10 may be employed to counter this effect. This would be a personalized solution depending upon which of the numerous neutralizing antibodies is causing the issue. For example, the energy-state may be femtovolt, the work-state may be to incite quantum decoherence of the target 16 or target zone 18 and the intent may be designing for complete removal, similar to artificial enzymes. As noted previously, quantum coherence may be set in femtovolt work state (covalent bonds set the intrinsic spin (spin-orbit)) which defines the energy holding the coherence. J-coupling is setting the charges of the coupling of the molecular structure (which defines how it will fold up, which defines how the energy is transferred through the structure).

A signal or function generator is a device that can produce various patterns of voltage at a variety of frequencies and amplitudes. While frequency and voltage are different things, a voltage with a 0 frequency is steady at a certain value which is also known as DC voltage. When the femtovolts energy-state is leveraged for quantum work-states including creating, electrons (particles, matter) through the solitons of the charged electron fields; the soliton magnitude (classically equal to the amplitude) is determined through the properly manipulated energy-pattern of the Qsphere vector coupled with the correct quantum energy-state. The energy-pattern in one example can be calculated through the target zone 18 mass or energy of the m/z mass spectrum. The energy-pattern of the Qsphere vector is what makes this solution target-specific. The target-tuned factors of the properly manipulated Qsphere vector coupled with the quantum energy-state that are then transferred to the artificial atoms 44, using those target-tuned factor values applied to the function generator 152 (as described below with respect to block 108). The Qsphere vector defined as the point that lies on the surface of the Qsphere.

Referring to FIG. 12, an alternative or second set-up 300 is shown for obtaining the intrinsic parameters and the custom design factor of the target 16 and target zone 18. Optionally, a Fourier transform may be taken of the mass spectrum 250 in order to elicit more information. Referring to FIG. 11, a Fourier transform 260 of the mass spectrum 250 is shown, with frequency (F) on the horizontal axis and amplitude (A) on the vertical axis. The Fourier transform 260 illustrates at least one mass spectrum peak 262 occurring in a respective band 264, which may have a mass spectrum peak at m/z of 375.

The calibration process may include running the sample 210 through the mass spectrometer 202 (or RF quadrupole spectrometer 302) to see if the target zone mass spectrum peak is removed or altered after exposure to the manipulating agent 12. If the target zone mass spectrum peak is not removed or altered, the calibration factor of the energy-pattern of the Qsphere vector and quantum energy-state is adjusted, and the process is repeated until the mass spectra peak of the target zone 18 is removed or altered.

In one embodiment, the target-tuned design factors for the energy-pattern ranged from 1-999 femtovolts or 1-999 picovolts. In one example, the calibration factor is 1 femtovolts per 100 volts. In another example, the calibration factor is 10 picovolts per 100 volts. The calibration factor may be specific to the target zone 18 and may vary based on the intent/usage of the manipulating agent 12 (inhibitor or treatment). In one example, the target 16 is a SARS-CoV-2 virus, the target zone 18 is the N-Protein, the target zone intent is neutralization of a virus in a viral infection. The intrinsic parameter of the energy-pattern and QSphere vector of the target 16 was identified with an Orbitrap mass spectrometer with an initial ion mass of 375 (mass spectrum peak at 375 m/z (and a final calibrated target zone value of 375 m/z)). The quantum work-state for neutralization is found in the energy-state of femtovolts, which correlates with an electron creation and entanglement rate. The target-tuned design factors of the electrons are then defined by the quantum energy-pattern of 3.75 femtovolts ($3.75 \times 10^{-15}$ V) which defines a Qsphere quantum work-state equal to a phase-flip and incites decoherence by decoupling the coherent system and the gluons which are holding the structure in quantum coherence. The target tuned artificial atoms 44 are generated and transferred with the DC powered (constant polarity) function generator 152 with magnitude equal to the constant amplitude=3.75 femtovolts and frequency=0. The wave-type may be sawtooth, which correlates with soliton waves and standing waves of packets of energy. In one example the target 16 is a SARS-CoV-2 virus, the target zone is the S-Protein (responsible for the ligand-receptor attachment and viral replication), the target zone intent is structure dysfunction to upregulate the immune system. In one example, the energy-pattern of the target zone 18 was identified with the Resonance Recognition Model with and energy-pattern and Qsphere vector=0.312 of the energy-state equal to microvolts with aninitial molecular target of energy transfter between coherent systems and between interacting biomoleculrs of 0.312 teraherttz (and a final calibrated value of 0.300 terahertz.) The energy-state of picovolts contains the work-state that provides the dysfunction (manipulation) factor which correlates to setting the atoms charge within the functional group, which causes the structure to fold up incorrectly by manipulating the hydroxyl bond order. The target-tuned design factors of the electrons are then defined by E=30 picoVolts ($3.0 \times 10^{-12}$ V) to incite bit-flips and induce the hydroxyl bonds to be set incorrectly. The target-tuned artificial atoms 44 are generated (and may be transferred) with a DC powered function generator 52, with E=magnitude (amplitude) and frequency=0, with the use of a sawtooth wave-type, which correlates with standing waves of packets of energy. The calibrations of the Qsphere energy-pattern and energy-state design factors may vary due to a variety of factors including target zone diameter, target zone size, target zone age, target contents, target genome size, target zone geometric configuration, and target zone shape.

Per block 106 of FIG. 9, the method 100 includes preparing a container 46 to carry the unquantized target-tuned electrons E. In the embodiment shown, the container 46 chosen to carry the unquantized target-tuned electrons E is a structurally engineered tunable clathrate structure 400, (shown in FIG. 13) with a crystalline, lattice structure that is engineered to take on the properties of an empty, tunable superconductor quantum dot. The engineered clathrate structure 400 may be an engineered clathrate hydrate 400. More specifically the container 46 which is a tunable clathrate (void of guest molecule) is also considered an engineered, stable and tunable supramolecule water cluster that maintains quantum coherent hydrogen bonds without collapsing. A water cluster is a discrete hydrogen bonded assembly or cluster of molecules of water. Many such clusters have been predicted by theoretical models (in silico), and some have been detected experimentally in various context such as ice, and bulk liquid water, in the gas phase, in dilute mixtures with non-polar solvents, and as water of hydration in crystal lattices (clathrate crystals.) However, establishing supramolecule structures in bulk water is difficult because of their extremely short lifetime with the hydrogen bonds continually breaking and reforming at timescales faster than 200 femtoseconds. Clathrate hydrates (clathrates or hydrates) are crystalline water-based solids physically resembling ice in which small non-polar molecules (typically gases), or polar molecules are trapped inside the cages of hydrogen bonded, frozen water molecules. Clathrate hydrates are clathrate compounds in which the host molecule is water and the guest molecule is typically a gas or a liquid. The clathrate is structurally engineered to be tunable such that it does not contain a guest molecule but instead has a hollow interior portion. The Meissner effect superconductor properties of the clathrate hydrate structure provide the collective and quantum coherent functioning of the electron-positron pairs, providing both the positive inner lining L1 (to contain and hold the added energy of the electron field F, see FIG. 16) and the negative outer lining L2 (see FIG. 16) to repel any outside interference. The hollow center and maintained lining of positive charges provides the opportunity to add and transport additional tunable energy in the form of electron fields.

The existence of the crystalline structure of clathrate hydrates, cytosolic proteins is only possible due to their internal molecule which holds their molecular structure in existence. Without these internal molecules, their structure would also be impossible and collapse. Ice holds its crystalline structure due to its solid nature, as do other crystal solids. The superconductor quantum dot (sQD) has three unique defining features that provide this molecular crystalline structure with its value. The first is the maintained existence of this stable and liquid crystalline structure, which is void of the center molecule, is made possible by the induced electron-positron coherent pairing. The second property, the electron-positron pairing combined with the lack of the internal molecule provides the superconductor properties of a vacuum interior that allows energy to be held and retained without degradation or interference of outside fields. The third, the first two properties combined with the lack of interior molecule allows the weak and flexible hydrogen bonds to be exploited. Without the rigid core, the hydrogen bond angles can be manipulated and distorted to both capture and expose/deliver energy. Crystalline solids, as well as the clathrate hydrates and cytosol proteins do not have the ability for their weak hydrogen bonds to be exploited and manipulated due to their rigid structure. It is the combination of these properties that provide the sQD with the unique traits of being a stable, coherent superconductor structure that has the ability to capture, retain, transport, and deliver target-tuned energy.

Due to the purposefully engineered tunable clathrate structure and super conductor properties, the quantized target-tuned electrons Q are held suspended in three-dimension by the positron lining L1 within the "cage" and do not interact with it. Thus, the structurally engineered clathrates in the container 46 do not contain a guest molecule but instead are embedded with the quantized target-tuned electrons Q. This allows the custom designed energy to be quantized into engineered and target-tuned artificial atoms 44. The target-tuned artificial atoms 44 thus imbibe superconductor properties, allowing the energy to flow without any electrical resistance (without the change or loss of energy) and with all magnetic flux fields being expelled. Additionally, the hydrogen bonds within the specific H2O molecule of the clathrate structure have the ability to change their angle when vibrated or shaken which disturbs the entire clathrate structure including the H—H bonds to expose the energy of the custom designed and discrete electrons (quantum electron fields). This is similar in concept to when regular quantum dots (QDs) are exposed to ultraviolet light. The exposure to the ultraviolet light disturbs the QD structure slightly to expose the photons of the electromagnetic field for measurement of their extremely specific wavelength and color. The wavelength and color combination being based on their custom designed and discrete electrons and energy levels. For instance, superconductor quantum dots (referred to hereinafter as "sQD") can be thought of and utilized within superconducting circuits for any industry. These sQDs provide the advantage of being room-temperature operable, multi-qubit (each dot within the molecular structure is considered a qubit and with each qubit, you add more power/magnitude), energy-tunable (such as adding custom designed energy), and quantum coherent (stable, with delocalized electrons). The quantum coherent pairs of electrons and positrons in superconductors are called Cooper pairs and act as one particle. The relevant fact is that the energy levels of the Cooper pairs in a superconducting loop such as one that contains a 'Josephson junction' are discrete and can be used to encode qubits. Superconductivity provides extraordinary capabilities for electric circuits. With elimination of conductor resistance, there is no power loss or inefficiency in electric power systems due to stray resistances. Electric motors can be made almost (100%) efficient. Components such as capacitors and inductors, whose ideal characteristics are normally spoiled by inherent wire resistances, can be made ideal in a practical sense. In quantum computing, pairs of quantum dots such as in Josephson junctions can serve as a single basic element in a quantum logic device, called a quantum bit or a qubit in which measuring the spin allows for the building of logical gates.

The sQD structure size and number of atoms (which define magnitude or power) can be configured based on the electromagnetic induction exposure time. The size of the sQD (hydrate structure) is exposure time dependent, with a longer exposure time creating a larger structure. The electrons are created within the femtovolt energy-state (with specific energy-density) and the entanglement (intrinsic spin or spin-orbit) is set. With the application of the magnetic field, this realigns (re-sets) electrons and their entanglements according to the orientation of the magnets. It is the creation of the two spin-states (spin-orbit) based on the magnetic poles that replicates the femtovolt and picovolt energy states for the creation of a coherent system, including the reversal of electron spin to create the positron pairs required for the superconductor properties.

The magnetic realignment process discussed above may be employed to reset electron intrinsic spin and reverse spin for half of the electrons to create positrons and cooper pairs. The magnetic realignment process may be employed to create sQDs for crystalline structures and more generally for the following: (1) superconductor materials (artificial superconductors): to hold, carry, and deliver energy; and (2) multi-qubit materials (artificial multi-qubits), including coherent multi-particle structure with a specific and known energy-pattern that can be controlled and manipulated. The magnetic realignment process may be used to create suprahydrates (e.g., artificial cytosolic proteins) or crystal structures that may be utilized within a body for quantum processes, similar to a qubit. The magnetic realignment process may be used to create crystals for other uses such as fullerenes, quantum dots, gems, etc. As understood by those skilled in the art, fullerenes are allotropes of carbon whose molecule consists of carbon atoms connected by single and double bonds so as to form a closed or partially closed mesh, with fused rings of five to seven atoms. Fullerenes may incorporate many different define different shapes, including hollow spheres and tubes. The sQD transports energy across physical energy-states to collapse into energy-states. This is not dissimilar to how fullerene components are utilized to transport materials across various chemical states. For example, the central carbonyl cage of the 6-glutamate carbonyl groups is utilized in the transportation of insulin crystals, with the central carbonyl cage believed to be conserved through evolution back through hagfish. Because the insulin receptor only binds insulin monomers, if the hexamers dissociated to monomers right after leaving the pancreas, most of the insulin would be bound by insulin receptors in the liver and other central organs, and our distal tissues would see very little insulin, if any. (http://www.s-cirp.org/reference/ReferencesPaper.aspx?ReferenceID=1921201, https://pubs.acs.org/doi/10.1021/bi00328a027)

Figure 13:
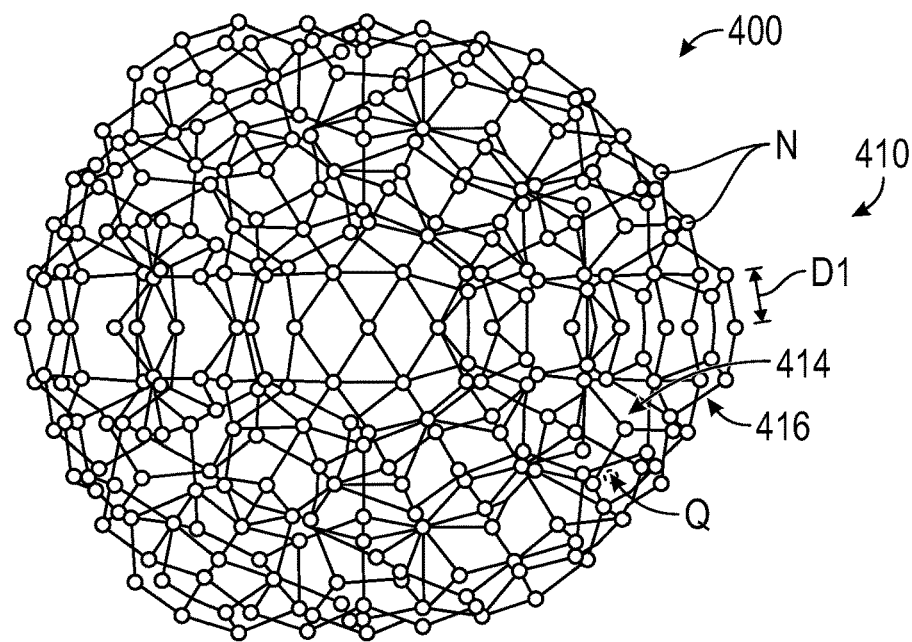
FIG. 13 is a schematic fragmentary diagram of an engineered tunable clathrate structure (in an original state) employable by the system of FIGS. 1 and 2.

Per block 106 of FIG. 9, the method 100 includes preparing a container 46 to carry the quantized target-tuned electrons Q (generated and transferred in block 108). A solution of distilled water is exposed to a first predefined magnetic field for a first predefined time to incite quantum coherence (first electromagnetic induction) to form an engineered tunable clathrate structure 400, which functions as a container 46. The first predefined magnetic field may be provided via the magnetic field generator 154 of FIG. 8, with magnets in a specific orientation, e.g. north to south. The solution of distilled water is pure and absent of any potential contaminants. In one example, the field strength is 4600 Gauss, and the predefined time is 15 minutes. An example of an engineered tunable clathrate structure 400 is shown in FIG. 13, in the form of a tetrahedral clathrate. In some embodiments, the engineered clathrate structure 400 is fully or at least partially composed of urea. In other embodiments, the engineered structure is any structure that can be manipulated to induce quantum coherence and the formation of hydrogen-hydrogen (H—H) bonds.

Referring to FIG. 13, the engineered tunable clathrate structure 400 is shown in an original state 410. The engineered clathrate structure 400 has a lattice or crystalline structure 45 with a plurality of nodes N defining a hollow interior portion 414 and an exterior portion 416. The crystalline structure 45 can hold the charge in a stable environment within the "cubes" created after the engineered clathrate structure 400 is formed. The exposure to the first predefined magnetic field is continued until the hollow interior portion 414 of the engineered clathrate structure 400 is at least partially lined with positive charges and the exterior portion 416 is at least partially lined with negative charges. The creation of the engineered clathrate structure 400 through this process lines the exterior portion 416 of the clathrate structure with negative electrons (electrons), while the hollow interior portion 414 of the structure is lined with positive electrons or positrons. This process creates a mega superconductor structure of clathrates in which this quantum coherent collective functioning of the electrons (positive and/or negative) excludes an external magnetic field and maintains an impenetrable status. Here, electrons are allowed to flow without resistance forever; this Meissner effect of superconductivity is experienced at room temperature.

Once the engineered tunable clathrate structure 400 is formed (per block 106), (in some embodiments, the structure 400 may be a hydrate or clathrate hydrate), the unquantized target-tuned electron E (having respective associated electric fields) is generated and transferred into the solution, (assisted by the application of a first vibration described below) for capturing and quantizing them as quantized target-tuned electrons QF into the engineered clathrate structure 400, per block 108. As shown in FIG. 16, the quantized target-tuned electrons Q (having respective associated electric fields) are stored with the container 46 in order to form the artificial atom 44. The engineered clathrate structure 400 is a "superconductor" quantum dot (sQD), with each clathrate or dot being a tiny man-made crystal with the superconductor properties. The term "quantum dot" refers to a substantially ball-shaped, cube-shaped, or cluster-shaped structure and having a width/diameter small enough (typically on the order of 20 nm or less) to support discrete or quantized allowed energy levels. But quantum dots are made of semiconductor materials. The engineered container, due to the properties of the supramolecule water cluster and "water ordering" of the clathrate around a hydrophobic particle in which the structure provides the crystal or lattice structure with Hydrogen-Hydrogen bonds and the particle provides the stability for the maintained structure and acts as one of the key driving forces for protein folding and the formation of functional multiprotein aggregates. It also sustains the self-assembly of lipid membranes and matching of hydrophobic surfaces often observed in protein-ligand binding.

Hydrophobic interactions are a dominant force in molecular biology. They mimic the more common small water clusters and are important as they provide the safety of the container. Small water molecule clusters constantly activate human cells and carry more minerals and oxygen to cells. In another embodiment, the sQDs are provided as a suprahydrate water structure tuned to improve molecular functioning within cells which comprise 70% water and utilize the molecular backbone of the covalent bonds and the power poles of the H—H bonds to increase cellular efficiencies and communications, such as increasing DNA polymerase functioning (DNA error correcting), increasing protein folding, increasing protein-ligand binding, supporting gap junctions, increasing external and internal cellular communication.

Figure 14:
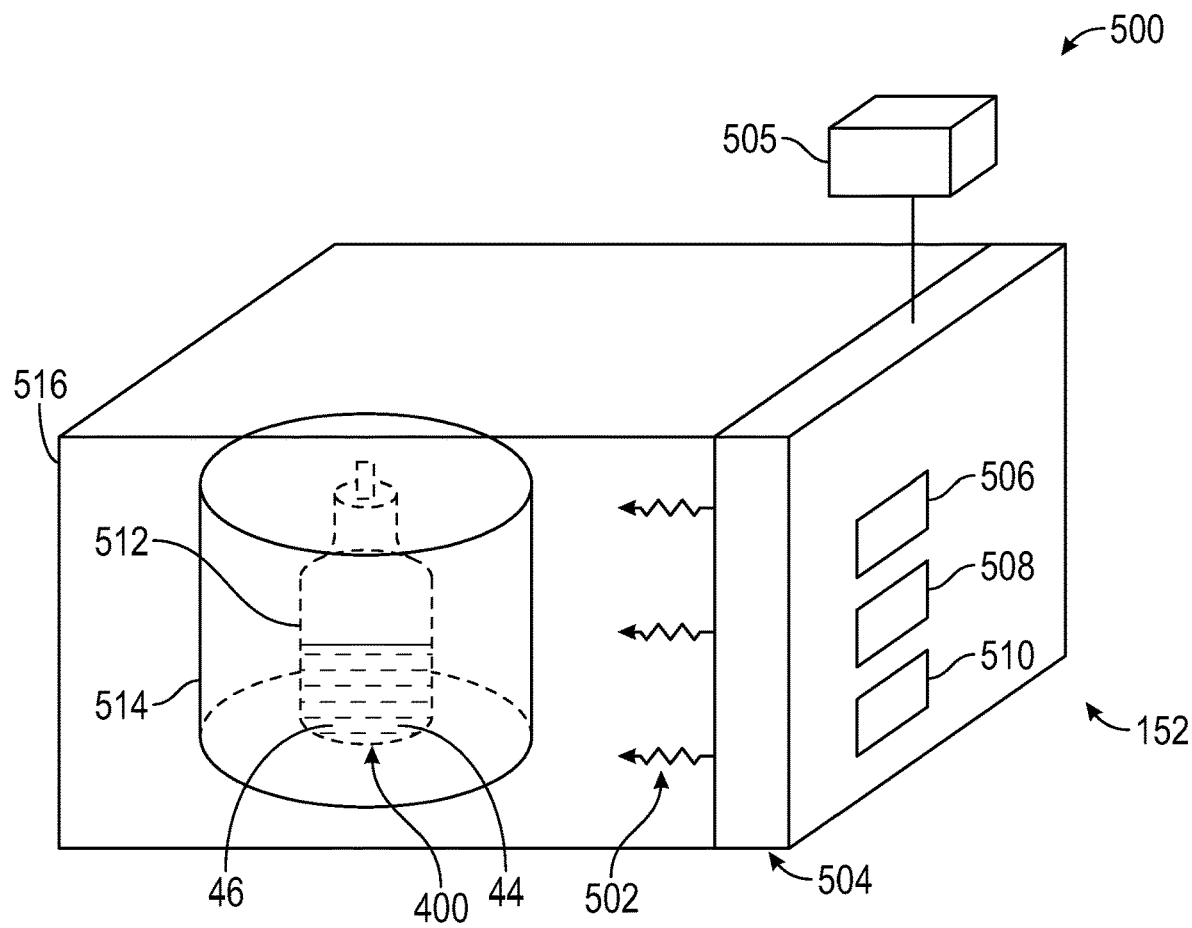
FIG. 14 is a schematic diagram of an apparatus employable by the system of FIGS. 1 and 8, the apparatus having a function generator.
Figure 15:
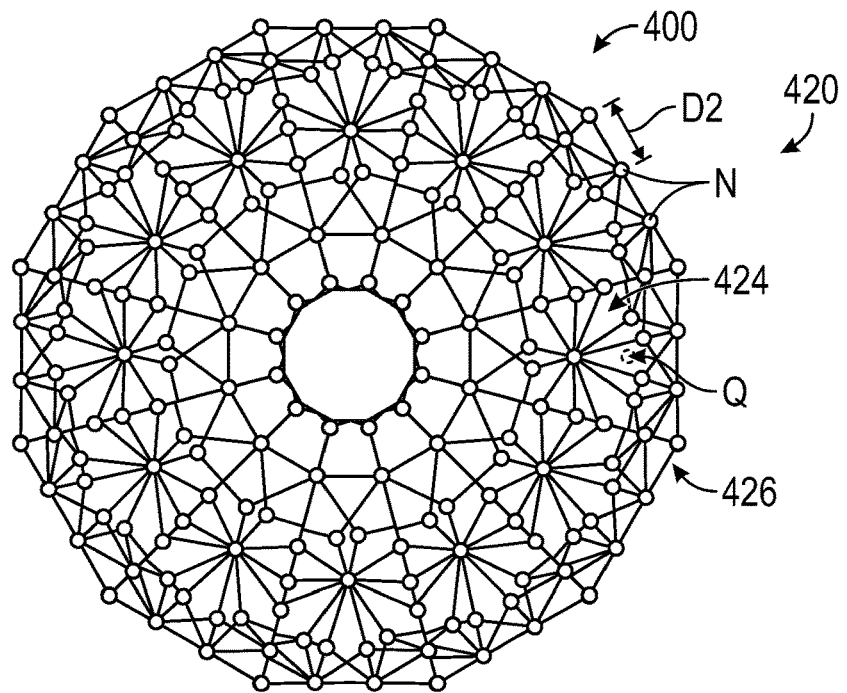
FIG. 15 is a schematic fragmentary diagram of the engineered tunable clathrate structure of FIG. 14, in a compressed state.

Per block 108 of FIG. 9, the method 100 includes generating the quantized target-tuned electrons Q based in part on the target-tuned design factors obtained in block 104. The target-tuned artificial atoms are fully quantized down to the quantum field which are more fundamental than elementary particles. FIG. 14 shows an apparatus 500 for generating and transferring the target-tuned artificial atoms 44 in the container 46. The apparatus 500 includes a function generator 152 (which may be direct current powered) adapted to produce waveforms 502 having a specific voltage patterns via a waveform generator 504 and power source 505. The power source 505 may be any type of source for generating electrical energy available to those skilled in the art. In one example, the power source 505 is a DC voltage power supply.

As understood by those skilled in the art, a function generator 152 (also known as a signal generator) is an electronic device or signal source used to generate various patterns of voltage at a variety of frequencies and amplitudes (magnitudes.) The waveforms may be in the shape of a sine wave, square wave, triangular wave, sawtooth shaped and other shapes. While frequency and voltage are different things, a voltage with a 0 frequency is steady at a certain value with a constant polarity which is also known as DC voltage and a requirement for low-level energy. The function generator 152 may include respective controls such as first setting 506, second setting 508, third setting 510 to control the frequency, amplitude (magnitude), and wave type of the waveform 502, respectively. In other embodiments, the function generator is a femtowatt laser.

In the embodiment shown, the waveforms 502 are based on target-tuned soliton energy of DC voltage, with the amplitude (magnitude) setting (first setting 506) at the target-tuned design factor (from block 104). In mathematics and physics, a classical soliton or solitary wave is a wave that behaves like a "particle". It is a self-reinforcing wave packet that maintains its shape while it propagates at a constant velocity. Solitons are caused by a cancellation of nonlinear and dispersive effects in the medium. (Dispersive effects are a property of certain systems where the speed of a wave depends on its frequency.) Solitons are the solutions of a widespread class of weakly nonlinear dispersive partial differential equations describing physical systems. Solitons have been described as almost lossless energy transfer in biomolecular chains or lattices and atomic nuclei as wave-like propagations of coupled conformational and electronic disturbances. Solitons are more like a biophysical (as encountered with DC voltage) packet than an electromagnetic wave, due to electromagnetic waves being affected by $E=MC2$. This allows the arcane quantum mechanics concept of collapsing the wave and going from DC voltage soliton energy to electromagnetic energy. The target-tuned solitons (which can be DC voltage solitons) are employed to generate the target-tuned electrons (quanta of electron fields.) Generating the target-tuned artificial atoms 44 may be likened (in a classical sense) to generating a charged electron field having respective waves and inducing wave oscillation of the respective waves at a magnitude determined by the intrinsic parameter and the target-tuned design factors. (It is understood that the term "waves" is employed here as a classical analogy for understanding and not as a strict description). For non-classical quantum field purposes, utilizing quantum field theory and the standing ripples of the quantum electron field allows for the "creation" and "destruction" of target-tuned mass (also referred to as matter and anti-matter.) The creation and destruction of mass is possible because quantum field theory, in a coherent structure, does not deal with the probabilities of something occurring (wave-particle duality) like classical quantum mechanics. With quantum field theory, target-tuned solitons are employed to excite the electron field for the purposes of creating a quantum electron field (E) and creating electrons as defined by soliton DC where E=m, which defines the magnitude (amplitude) to create the unquantized target-tuned electrons E (as defined in particle physics as the 'anti-matter.') In the terms of having the ability to "collapse the wave function". Generating the target-tuned artificial atoms 44 excites the standing charge of the inherent electron field that exists all around us. When the electron field is excited, much like fields have waves the excitation induces ripples with packets of standing energy whose intensity is determined by the defined magnitude (amplitude) of the field ripple determined by the target-tuned design factors. These packets of standing energy are viewed as electrons in the subatomic particle world.

Referring to FIG. 14, the engineered tunable clathrate structure 400 may be placed in a vessel 512 within a frequency transfer device 514. The frequency transfer device 514 is sourced by direct current (DC) power to eliminate the low-level interference introduced by alternating current power sources. DC power provides constant polarity and the electron/charges only move in one direction. In AC (alternating current) the electrons/charges slosh back and forth continuously. The frequency transfer device 514 is composed of a good conductor of electricity. In one example, the frequency transfer device 514 is a copper container or a set of copper plates. The vessel 512 may be fully or partially encapsulated by the frequency transfer device 514. The voltage transfer device 514 may be embedded within the function generator 152 or positioned in proximity to it, inside a housing 516. The function generator 152 may be adapted to output any voltage, in this embodiment femtovolts or picovolts are output by incorporating variable resistance. The resistance is varied until the desired strength (including for example femtovolts or picovolts) is obtained. In one example, the target-tuned electrons area are in the quantum energy state equal to femtovolts ($1\times10^{-15}$ through $1\times10^{-18}$ volts). In another example, the target-tuned electron are in the quantum energy state equal to picovolts ($1\times10^{-13}$ through $1\times10^{-14}$ volts). In another example, the target-tuned electrons are in the quantum energy state equal to nanovolts ($1\times10^{-9}$ through $1\times10^{-11}$ volts).

Once the solution 12 is prepped with the container 46 the solution is inducted with the quantized target-tuned electrons Q (having respective associated electric fields) followed by the application of rapid vibration or agitation, referred to herein as the first vibration, to capture the quantized target-tuned electrons Q within the container 46 (e.g. engineered clathrate structure 400). The first vibration may include agitating the solution for a predefined time, via a vibrating or shaking device. In one example, the shaking device is a Heidolph Instruments Multi Reax Shaker. The following settings may be employed: the "Motion Type" as "Vibrating," RPM as 500 rpm and the time set as 5 seconds (see https://heidolph-instruments.com/en/products/Shakers-Mixers/Multi-Reax~p1189). The first vibration is intended to capture and suspend the quantized target-tuned electrons Q beneath the inner lining L1 of positive charges of the container 46. The first vibration distorts the container 46 (e.g. engineered clathrate structure 400) by rapidly cycling the underlying $H_2O$ bond angles between 104.5 and 106 degrees, enabling capturing of the quantized target-tuned electrons Q to the inner lining L1 of the container 46. This internal electron-electron bonding/pairing is what holds and transports the new energy state in the material. The target-tuned artificial atoms 44 are quantized electron, which lack a nucleus but are contained by a positive force. The electrons are created as target-tuned electrons per the requirement of a specific object. The superconductive status when bonds are stretched and distorted through the agitations may enable the quantum electron fields contained within the target-tuned artificial atoms 44 to instantly expose the electron fields which surrounds the quantized target-tuned electrons Q (having respective associated electron fields) through the subject 14 to interfere with the quantum coherence of a target zone 18.

The transfer of the target-tuned artificial atoms 44 may be validated through a properly designed quality control process. For one embodiment, the removal of a mass spectrum peak (sometimes referred to as a marker), for example, the peak of a target or specific target zone on a mass spectrum 250. Such a marker disappears when the target 16 or target zone 18 is removed or disabled through the action of the target-tuned artificial atoms 44. This disappearance of the mass spectrum peak or marker is employed for quality control purposes. The system 10 may include a validation process for determining if a mass spectrum peak correlated to the target zone 18 is removed. If the mass spectrum peak correlated to the target zone 18 or target 16 is not removed or adjusted as designed, the calibration factor (energy-pattern of the Qsphere vector in conjunction with the quantum energy-state) is adjusted and the validation process is repeated. This is repeated until the mass spectrum peak correlated to the target zone is removed or adjusted as designed. In another embodiment, the target-tuned artificial atoms 44 may be validated through in-vitro or in-vivo testing to validate the inhibition for the target zone 18 to dock in the subject 12 (host) receptor cell and replicate. If the correct inhibition of the target zone 18 is not achieved, the calibration factor should be adjusted and the validation process repeated. An example of a quality control test is illustrated in FIG. 17. FIG. 17 shows a mass spectrum of a marker related to the human rhinovirus. An example antiviral treatment binds to the viral capsid and results in the suppression of the marker. This suppression may be monitored via mass spectrometry. FIG. 17 shows the peak 602 of a viral capsid protein and the peak 604 of the viral RNA. Portion 606 of the mass spectrum indicates very little digestion observed and the marker remaining, while portion 608 showed significant digestion and the marker being suppressed. In yet another embodiment, when the target zone 18 is constructed of a protein, the target-tuned artificial atoms may be validated through proteome sequencing to determine if the bond order (and target zone 16) have been rearranged. Other methods available to those skilled in the art may be employed. Additionally, mass spectrum analysis may be employed for diagnosing the presence of an infection (e.g. for S-protein testing in-vivo). FIG. 18 shows an example mass spectrum of intensity (vertical axis) versus mass to charge ratio (m/z on the horizontal axis) for a strain of influenza. Control trace 650 shows the spectrum for a control group of uninfected cells. First trace 652 illustrates multiple peaks, indicating the presence of influenza B Neqas-MDCK SIAT 1 infected cells. Second trace 654 illustrates multiple peaks, indicating the presence of influenza A ATCC-MDCK 1 SIAT 1 infected cells.

Per block 110 of FIG. 9, the method 100 optionally includes stabilizing the engineered clathrate structure 400 (containing the target-tuned electron interference field F) from the original state 410 to a compressed state 420 (shown in FIG. 15) via a second electromagnetic induction. Referring to FIG. 8, the second predefined magnetic field may be provided by the magnetic field generator 154 or a secondary generator 156. After electrical induction with the target-tuned artificial atoms 44 in block 108, the solution (with the engineered clathrate structure 400 and artificial atoms 44) is exposed to a second electromagnetic induction (with a second predefined magnetic field for example) to stabilize the energy states of the artificial atoms 44. This stabilization process compresses the engineered clathrate structure 400 in the original state 410 (of FIG. 13) to a compressed state 420 (shown in FIG. 15). The reduction of the interatomic spacing further compresses and strengthens the electron-electron bonding and superconductivity in this engineered nanoparticle. With the compressed angstrom size, more clathrates (dots) fit in the same space and hence more energy is held. Referring to FIG. 15, in the compressed state 420, the engineered clathrate structure 400 has a lattice or crystalline structure with a plurality of nodes N defining a hollow interior portion 424 and an exterior portion 426. The plurality of nodes N are separated by a second interatomic spacing D2. The second interatomic spacing D2 is less than the first interatomic spacing D 1.

In one embodiment, the original state 410 is a tetrahedral clathrate and the compressed state 420 is a hexa-kai-decahedral clathrate. Here the first interatomic spacing D1 and the second interatomic spacing D2 are approximately 4.68 Angstrom and approximately 3.91 Angstrom, respectively. The interatomic spacing may vary throughout the engineered clathrate structure 400. The sizes listed are for the portions that are best able to hold the introduced energy (electrons) due to their internal lining L1 of positive charge (see FIG. 16). The interatomic spacing measurements may be obtained via x-ray interferometry. The reduction of the interatomic spacing compresses and strengthens the electron-electron bonding and superconductivity. With the compressed Angstrom size, the smaller clathrates (dots) are packed more densely and contain more surface area and more energy is held. The compressed state 420 is thus more stable relative to the original state 410. The increased energy of the compressed state 420 also results in improved efficacy. Efficacy is driven by bioavailability, which is in turn driven from particle size with research showing particle size is related to kinetic solubility rather than equilibrium solubility. With the raw numbers of 4.68 Å and the magnetized or compressed version of 3.91 Å, there is a 17% reduction in size resulting in 20% more efficacy.

Per block 112 of FIG. 9, the method 100 includes activating the target-tuned artificial atoms 44, in other words, converting the target-tuned artificial atoms 44 to a usable form. Referring to FIG. 1, the target-tuned artificial atoms 44 may be placed in a container or bottle 48 and a second vibration is applied, i.e. the target-tuned artificial atoms 44 are agitated or succussed or shaken or tapped for a specific number of times. Referring to FIG. 16, the second vibration serves to at least partially expose the quantized target-tuned electrons QF within the target-tuned artificial atoms 44, which are held by the inner lining L1 in the container 46. The second vibration is adapted to increase the bond angle of the hydrogen-hydrogen bond in the engineered clathrate structure 400. In one example, the bond angle of the water molecules increases from approximately 104.5 to a maximum of 106 as a result of the second vibration, enabling exposures of the quantized target-tuned electrons Q and the respective associated electron fields surrounding them. In one embodiment, the target-tuned artificial atoms 44 are tapped exactly ten times. The manipulating agent 12 is then delivered to the subject 14. The method of delivery may be oral ingestion, nasal ingestion, topical application or inhalation in a nebulized or inhaler form. The method of delivery may include injection or IV (intravenous) and other suitable methods. In one example, the disruptive agent 12 is applied sublingual to the subject 14. The bottle 48 and other materials in contact with the manipulating agent 12 (such as a dropper for example) are composed of an inert material in order to avoid interference. In one embodiment, the bottle 48 is composed of glass. Additionally, the bottle 48 with the manipulating agent 12 should not be exposed to ionizing radiation, such as x-rays, during shipping. Alternatively, as shown by block 114 and line 109 of FIG. 9, the manipulating agent 12 may comprise of the quantized target-tuned electrons Q delivered directly to the target 16, without a solution or container 46. The method of delivery may include direct application of electron field in methods such as dialysis, direct body contact such as a cuff and other suitable methods.

The manipulating agent 12 may be configured based on the specifics of the target zone 18 and the intent/usage in question. In some embodiments, the usage of the manipulating agent 12 is as an antigen inhibitor, a substance which slows down or prevents a particular chemical reaction or other process, or which reduces the activity of a particular reactant, catalyst, or enzyme. In other embodiments, the usage of the manipulating agent 12 performs similar to a neutralizing, temporary antibody, a substance which supports counteracting or neutralizing an antigen for the treatment of a current infection. In some embodiments, the manipulating agent 12 is an artificial enzyme intended to remove or 'cut' a substance or target zone from a target.

As noted previously, referring to FIG. 1, the target 16 may be a virus having at least one receptor viral docking structure 28, such as spike protein 30 (sometimes referred to as S-Protein). In some embodiments, the manipulating agent 12 is adapted to inhibit at least one receptor viral docking structure 28, thereby preventing replication of the virus. This allows the body of the subject 14 to identify the virus and create antibodies, while limiting the ability of the virus to reproduce. Here, daily dosing is most likely required. In one example, the target 16 is SARS-CoV-2, the target zone 18 is the spike protein 30, the intrinsic parameter of the target zone is the energy-pattern and Qsphere vector of mass of 312 (312 m/z) with a final, calibrated target-tuned field factor defining the quantized target-tuned electrons Q and the artificial atoms 44 being characterized by 30 picoVolts and pico energy-state to disrupt bond vibration and setting of charges.

In other embodiments (as noted previously), the manipulating agent 12 is adapted to target the nucleocapsid protein 36 (or N-protein) for treatment of an infection. Targeting the nucleocapsid protein 36 physically removes covalent bonds by removing the gluons holding the electron shell together which reduces the structure down into its base amino acids (proteins are made of amino acids strung together with chemical bonds) which can be repurposed by the body of the subject 14. In one example, the target 16 is a coronavirus (such as SARS-CoV-2), the target zone 18 is the nucleocapsid protein 36, the intrinsic parameter of the full target is mass of 430 (430 m/z) of the macro-dimension energy-state of volts and intracellular energy transfer with the unquantized target-tuned electrons E and artificial atoms 44 being characterized with an energy-pattern of 3.75 femtovolts.

In one method, the manipulating agent 12 interferes with the quantum coherence of the target 16 via inciting quantum decoherence. Quantum decoherence is seen when a quantum coherent system encounters an interference field that shifts the spin-orbit of the quantum coherence. While it appears that chemical bonds of the target zone 18 will break, decoherence does not really break chemical bonds in the target zone 18; with quantum interference the excited electron fields, that are bundling up energy into matter (electrons) in the ripples, are flattened. This is generally termed a collapse in the wave function. However, in technical sense it does not generate actual wave-function collapse. It only provides an explanation for apparent wave-function collapse as the quantum nature of the system 'leaks' back into the quantum field. That is, components of the quantum field ripples are decoupled from a coherent system and acquire phases from their immediate surroundings. The energy is dispersed back into the quarks (atoms) within the underlying quantum electron field in the ultra-micro dimension. In essence, the gluons holding the electron "shell" together are physically removed, which is neither endothermic nor exothermic. With the application of quantum field theory, this is not a true collapse of the wave-function (also referred to as annihilation of energy due to anti-particle collision as defined within particle physics) because with the application of quantum field theory and interference fields the (now flattened, de-excited) electron field has the ability to reform 'electrons' in the future. With particle physics in order to study antimatter, it has to be made. When enough energy is squeezed into a very small space, such as high-energy particle collisions, particle-antiparticle pairs are produced simultaneously. It is at the point when energy transforms into mass, that both matter and antimatter are created in equal amounts. With the application of quantum field theory one can work with the fundamental fields, most specifically the electron field and quark field which are defined as our only usable mass fields (also referred to as matter field.) Coupling this application with operating in the ultra-microworld (below 14.1 Angstrom), then energy becomes equivalent to mass. This allows the creation of "anti-particles or anti-matter" without having to go through high-energy particle collision. Additionally, since the mass or particle (of the anti-mass or anti-particle) already exists in the form of a quantum coherence field, once you define the properties of the quantum coherence of the electron field you can create the exact 'anti-matter' that is needed to incite decoherence. Quantum field theory displaced the Dirac sea theory by turning a positron into a real particle rather than the absence of a particle. This then follows Dirac's hole theory that if one operates in the correct quantum-time domain where that coherence exists, one may fill and borrow all of the exact sand that is needed without anyone knowing. To incite decoherence, the energy states of the electron field are exploring and looking for their correct "hole" (positron or electron). This may be visualized as a specific positive charge looking for a specific negative charge. In terms of a classical analogy, when two wave fields are superposed, their wave crests may add up (constructive interference), while the encounter of a crest and a trough tends to cancel the wave (destructive interference). Also as a classical analogy, in molecular orbitals the wave functions are three dimensional, and they combine with in-phase waves producing regions with a higher probability of electron density and out-of-phase waves producing nodes, or regions, of no electron density.

Presented below is a discussion of quantum tunneling relative to hydrogen bonds. Quantum tunneling supports the quantum superposition of the macroworld chemical work such as dipole swapping within enzymes, J coupling, functional group formation, DNA unzipping, and is at the foundation of diseases such as genetic polymorphisms. Quantum tunneling is supported through the dark quantum energy of the picovolt energy-state within the Quantum Energy Theory. Quantum tunneling plays an essential role in the quantum superposition (simultaneous sharing) of two or more quarks (atomic nucleus) in a quantum coherent system which forms the foundation of glueballs. Quantum tunneling also plays an essential role in the physical phenomena of nuclear fusion, wherein nuclear fusion is a reaction in which two or more atomic nuclei are combined to form one or more different atomic nuclei and subatomic particles (neutrons or protons.) Quantum tunneling typically occurs within hydrogen bonds and most specifically between hydrogen-hydrogen bonds. While hydrogen-hydrogen bonds are weak chemical bonds, they are the strong nuclear bonds within particle physics and store energy. In bonds that implement quantum tunneling, not only are atomic nuclei (quarks) shared simultaneously, but an additional sole electron is also shared simultaneously. The bonds that implement quantum tunneling coherently connects two or more quantum coherent groups and provides the energy transfer between the groups. This creates a larger quantum coherent group and establishes energy transfer. Quantum tunneling also determines the charge of an atom within a quantum coherent system for directing energy (switching the atom between glassy and crystalline states that represent the 0s and 1s of the binary code to store information), forms the blinking phenomena witnessed in hydrogen atoms and quantum dots, bit-flips within quantum computing, and electron-positron (matter-antimatter) pair creation (coherence and alignment). Quantum tunneling is also at the foundation of the 'quantum walk across a surface' which defines the way a quantum particle moves randomly from one point to another—which defines how free electrons naturally implement the Grover search algorithm when moving across the surface of certain crystals. The Grover search algorithm is defined as an algorithm that searches through a large database of entries, which is fundamental to everything from finding a telephone number to breaking cryptographic codes. In photosynthesis this 'quantum walk across a surface' was proposed as the most efficient mode of energy transfer so that multiple energy transfer options could be explored simultaneously, to find the correct and most efficient path of energy transfer. In the superposition of quantum energy-states, the quarks of the atomic nucleus operate in the picovolt energy-state. This energy-state controls the charge within the energy-pattern. With the dark quark energy-states pulling energy from the dark fields, as required, for the superposition of work. When decoherence is encountered and the gluons (being the force carriers of the quarks) are decoupled, the decoupling reaction causes the gluons to pull all mass and energy of the system back into the quarks of the nucleus to be redistributed to the dark fields. Quantum tunneling of the picovolt energy-state supports the superposition of macroworld chemical work such as dipole swapping within enzymes and is at the foundation of diseases such as some genetic polymorphisms.

In some embodiments, magnetic fields may be leveraged to manipulate dark quantum work properties (quantum coherence and quantum tunneling) to create a new quantum coherent molecule with a new energy-pattern, in the form of an artificial atom (crystal structure with a vacuum interior.) Quantum work is used to incite quantum coherence between hydrogen atoms within existing molecules through the physical formation of hydrogen-hydrogen bonds and incite quantum tunneling for the collective and coherent alignment of electron-positron pairs. Quantum work is defined as work that occurs in the quantum ultra-microworld and is physical work (and for instance, not chemical). The new molecule is a new quantum coherent molecule with collective functioning and alignment of electron-positron pairs in the form of a crystal structure with a hollow interior and vacuum. The vacuum and hydrogen-hydrogen bonds provide the ability to add, carry, and transport additional energy." Using equipment such as magnets, function generators and lasers, dark quantum energy can be created to transport and collapse into the macroworld to manipulate quantum energy-patterns (such as change molecules or breaking apart molecules) or dark quantum energy can be created to create a new quantum coherent molecule with a new energy-pattern (such as combining atoms or existing molecules.

In summary, the system 10 (via execution of the method 100) provides a manipulating agent 12 having target-tuned artificial atoms 44, which contain quantized target-tuned electrons Q (having respective associated electron fields) on a nanoscale level to deliberately manipulate the quantum coherence of the target 18. The method 100 determines and creates the target-tuned electron interference fields F, which may be stored or contained in the container 46 and delivered to the subject 14 in the form of target-tuned artificial atoms 44. The container 46 may be a structurally engineered tunable clathrate structure 400 which takes the form of a superconductor quantum dot. The container 46 may be engineered with linear (normal) water molecules whose quantum coherence has been deliberately manipulated to induce quantum coherence by the application of magnetic force fields to create a superconductor crystalline caged structure where the inside of the structure is hollow, but lined with positive charges (see inner lining L1 in FIG. 16) to hold the quantized, charged, energy levels and the exterior of the structure is lined with negative charges (see outer lining L2 in FIG. 16) to create an impenetrable magnetic field. The container 46 is a true quantum dot, in which the electrons have been contained by a positive structure providing the necessary requirements to quantize the energy levels. Alternatively, the target-tuned electron interference field E may be delivered directly to the subject 14, without a container 46.

Referring to FIG. 8, the system 10 may further include a user interface 158 operable by a user. The user interface 158 may include a touchscreen or other input device. The controller C may be configured to process signals to and from the user interface 158 and a display (not shown). The various components of the system 10 may be configured to communicate via a network 160, shown in FIG. 8. The network 160 may be a bi-directional bus implemented in various ways, such as for example, a serial communication bus in the form of a local area network. The local area network may include, but is not limited to, a Controller Area Network (CAN), a Controller Area Network with Flexible Data Rate (CAN-FD), Ethernet, WIFI, Bluetooth™ and other forms of data connection.

The embodiments presented herein relate generally to engineering and creating quantum coherent electron-positron pairs in or between molecules. More specifically, they relate to the creation of quantum coherent electron-positron molecules and material (including artificial atoms, super quantum dots, multi-qubits, crystals, lattice) from existing gas, liquid or solid molecules through spinQ-fusion for the intention of creating specific molecule structures for processes including information-energy storage, information-energy transportation, information-energy transfer or information-energy teleportation. This may include potential superconductor properties, depending on the structure and molecules utilized.

The embodiments presented herein relate generally to leveraging the dark quantum fields to manipulate the functioning of a target by physically manipulating the quantum properties of the target(s). More specifically, they relate to leveraging the dark quantum fields (including dark matter energy-patterns and dark energy-states in the form of for instance dark electron energy-patterns and dark quark energy-patterns). Leveraging the dark quantum fields may include one or more of the following: identifying visible-matter energy-patterns (including items such as energy, mass, electrons, charge, entanglement, coherence, discordance and Qsphere vectors), designing dark-matter energy-patterns (including items such energy-states (such as atto-volts, femtovolts, picovolts, nanovolts), work-states (such as dark interference, dark logical-structure order, Qsphere vectors, bit-manipulation, phase-manipulation).

Leveraging the dark quantum fields may include one or more of the following: creating dark-matter (including items such as dark target-tuned electrons and quark energy-states to strategically manipulate the quantum properties of a target or target zone); transporting dark matter as referred to in the above two paragraphs (including to protect the dark-matter energy-states from visible-matter interference); and delivering dark-matter/information (to re-localize and collapse into the visible-matter energy-states). The embodiments presented herein may be applied to manipulate the functioning (including items such as molecule existence, creation, order, shape, alignment, effectiveness, information, power or magnitude) of a target or target zone (including molecules such as solids, liquids, and gases) physically (without chemical or radiation work) or manipulating the dark quantum properties of the target(s) (including items such as discordance, coherence, entanglement, tunneling, gluons, electrons, and quarks).

The embodiments presented herein may be applied to the following applications (that include quantum coherence requirements for energy and information transfer): biotechnology devices (such as inducing quantum coherence through spinQ fusion); biotechnology health (such as superhydrates to repair and restore medical and or health dysfunctions related to items such as intracellular intercellular osmotic effects); electrical circuits and quantum computing hardware—including information and energy transfer, manipulation, and control (such as creating sQDs to form multi-qubits, cooper junctions and leveraging information for things such as dark error correction and dark manipulation).

The embodiments presented herein may be applied to quantum computing (including information transfer) such as software, cryptography, algorithms, security, defense (such as to manipulate unknown quantum requests, dark factoring, target-tuned cloning to maintain coherence); teleportation and telecommunications to delocalize and delocalize information and condensed matter for information transfer; new materials, molecules, and product/chemical formulations (such as new materials including dark electrons, crystalline structures, target-tuned artificial atoms, super quantum dots, superconductors (to reduce impact on animals, plants, endangered species such as sharks, for medical diagnostics, vaccines, supplements, etc.); and optics The controller C of FIG. 8 includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic medium, a CD-ROM, DVD, other optical medium, punch cards, paper tape, other physical medium with patterns of holes, a RAM, a PROM, an EPROM, a FLASH-EEPROM, other memory chip or cartridge, or other medium from which a computer can read.

Look-up tables, databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store may be included within a computing device employing a computer operating system such as one of those mentioned above and may be accessed via a network in one or more of a variety of manners. A file system may be accessible from a computer operating system and may include files stored in various formats. An RDBMS may employ the Structured Query Language (SQL) in addition to a language for creating, storing, editing, and executing stored procedures, such as the PL/SQL language mentioned above.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A method for manipulating quantum coherence in a target, the method comprising:
   identifying intrinsic parameters of the target, via a device;
   calculating target-tuned design factors based at least partially on the intrinsic parameters;
   generating unquantized target-tuned electrons using electromagnetic induction or electrical induction;
   preparing a container to carry target-tuned electrons, the container being composed of superconductor quantum dots, the container having a hollow interior portion generated via electromagnetic induction or magnetic induction;
   transferring the unquantized target-tuned electrons to the container to form target-tuned artificial atoms with quantized target-tuned electrons, the target-tuned artificial atoms defining discrete quantized energy states; and
   employing the target-tuned artificial atoms as a manipulating agent to manipulate the quantum coherence in the target.

2. The method of claim 1, wherein:
   at least one of the intrinsic parameters and the target-tuned design factors is a mass-to-charge ratio and the device is a mass spectrometer.

3. The method of claim 1, wherein:
   the target is a virus having at least one cellular membrane docking structure, the manipulating agent being adapted to inhibit at least one viral docking structure from docking into a cell receptor of a subject.

4. The method of claim 1, wherein:
   the container is an engineered clathrate hydrate that is tunable, the engineered clathrate hydrate having a plurality of nodes and the hollow interior portion having an inner lining of positive charges; and
   a target-tuned quantum electron field is stored in and contained by the inner lining of positive charges in the engineered clathrate hydrate.

5. The method of claim 1, wherein preparing the container includes:
   applying a first predetermined electromagnetic induction to a solution of distilled water to induce quantum coherence within the distilled water to form an engineered clathrate structure, via a magnetic field generator, the engineered clathrate structure having the hollow interior portion.

6. The method of claim 5, wherein inducting the container includes:

exposing the solution to an electromagnetic field or a magnetic field until the hollow interior portion of the engineered clathrate hydrate has an inner lining of positive charges and an exterior portion of the engineered clathrate hydrate is at least partially lined with negative charges and creating cooper pairs;

generating the unquantized target-tuned electrons within the solution via a frequency transfer device; and transferring the unquantized target-tuned electron field into the hollow interior portion of the engineered clathrate hydrate by applying a first vibration to the solution in order to attract and capture the unquantized target-tuned electrons within the inner lining of positive charges and form the quantized target-tuned electrons.

7. The method of claim 6, further comprising:

applying a second vibration to the target-tuned artificial atoms in order to expose the quantized target-tuned electrons from within the inner lining of positive charges in the engineered clathrate hydrate; and delivering the target-tuned artificial atoms as the manipulating agent to a subject.

8. The method of claim 7, wherein the second vibration includes exactly 10 vibrations.

9. The method of claim 6, wherein:

the engineered clathrate hydrate defines an original state with the plurality of nodes being separated by a first interatomic spacing and a compressed state with the plurality of nodes being separated by a second interatomic spacing; and the method further comprises stabilizing the engineered clathrate hydrate from an original state into a compressed state by exposing the original state to a second predefined magnetic field.

10. The method of claim 9, wherein the original state is a tetrahedral clathrate and the compressed state is a hexa-kaidecahedral clathrate.

11. The method of claim 9, wherein:

the first interatomic spacing and the second interatomic spacing are approximately 4.68 Angstrom and approximately 3.91 Angstrom, respectively.

12. The method of claim 10, wherein delivering the manipulating agent includes:

applying the manipulating agent sublingually to the subject.

13. The method of claim 10, wherein delivering the manipulating agent includes at least one of:

providing the manipulating agent through delivery routes within each of oral, sublingual, pulmonary, transdermal, ocular, otic, nasal, inhalation, vaginal, rectal, dialysis, nebulization, inhalation, cutaneous, subcutaneous, directly, and injection.

14. The method of claim 1, wherein the quantized target-tuned electrons are based on a calibration factor, the method further comprising:

determining if a mass spectrum peak correlated to the target zone is removed or adjusted, via a validation process; and adjusting the calibration factor and repeating the validation process if the target zone mass spectrum peak is not removed or adjusted.

15. The method of claim 1, wherein:
the target is a SARS-CoV-2 virus;
the target zone is the SARS-CoV-2 Nucleocapsid;
the intrinsic factor is an energy-pattern of a Qsphere vector of 375 volts based on an ion mass of 375 m/z; and
the target-tuned electron energy-pattern is characterized by the energy pattern of the Qsphere vector of 3.75 femtovolts ($3.75 \times 10^{-15}$ V) and a quantum energy-state of femtovolts.

16. The method of claim 1, wherein generating the target-tuned artificial atoms includes at least one of:
generating an attovolt quantum energy-state with a work-state in an attovolt region ($1 \times 10^{-18}$ volts through $1 \times 10^{-20}$);
generating a femtovolt quantum energy-state with a work-state in a femtovolt region ($1 \times 10^{-15}$ volts through $1 \times 10^{-17}$);
generating a picovolt quantum energy-state with a work-state in a picovolt region ($1 \times 10^{-12}$ volts through $1 \times 10^{-14}$); and
generating a nanovolt quantum energy-state and work state in the nanovolt region ($1 \times 10^{-9}$ through $1 \times 10^{-11}$);
and the method further includes: inducing a voltage of the electron field at a magnitude determined by the target-tuned design factor.

17. The method of claim 1, wherein generating the target-tuned artificial atoms includes:
adapting a function generator to generate target-tuned solitons, the target-tuned solitons being in a quantum energy-state less than 14.1 Angstroms.

18. The method of claim 1, wherein:
the target is a SARS-CoV-2 virus.

19. The method of claim 18, wherein:
the target zone is a nucleocapsid protein (N-protein), the manipulating agent being adapted to neutralize the SARS-CoV-2 virus in a viral infection.

20. The method of claim 18, wherein:
the target zone is a spike protein (S-protein), the manipulating agent being adapted to induce target zone structural bond reordering and shape change in the S-protein of the SARS-CoV-2 virus; and
the target-tuned electron energy-pattern is characterized by an energy pattern of about 30 picovolts ($3.0 \times 10^{-12}$ V) and a quantum energy-state of picovolts.

* * * * *